(12) United States Patent
Ashizawa et al.

(10) Patent No.: US 10,252,258 B2
(45) Date of Patent: Apr. 9, 2019

(54) METHOD FOR SEPARATING AND CONCENTRATING TARGET SUBSTANCE USING NOVEL CATIONIC GRAFT POLYMER

(71) Applicant: NITTO BOSEKI CO., LTD., Fukushima-shi, Fukushima (JP)

(72) Inventors: Kazuho Ashizawa, Koriyama (JP); Kenta Noda, Koriyama (JP); Koji Watanabe, Koriyama (JP); Yoko Teruuchi, Koriyama (JP); Masaru Bunya, Koriyama (JP)

(73) Assignee: NITTO BOSEKI CO., LTD., Fukushima-shi (JP)

( * ) Notice: Subject to any disclaimer, the term of this patent is extended or adjusted under 35 U.S.C. 154(b) by 242 days.

(21) Appl. No.: 15/120,820

(22) PCT Filed: Feb. 27, 2015

(86) PCT No.: PCT/JP2015/055892
§ 371 (c)(1),
(2) Date: Aug. 23, 2016

(87) PCT Pub. No.: WO2015/146487
PCT Pub. Date: Oct. 1, 2015

(65) Prior Publication Data
US 2016/0367979 A1 Dec. 22, 2016

(30) Foreign Application Priority Data

Mar. 24, 2014 (JP) .................................. 2014-060419
Mar. 24, 2014 (JP) .................................. 2014-060420

(51) Int. Cl.
*B01J 39/20* (2006.01)
*C08F 283/00* (2006.01)
(Continued)

(52) U.S. Cl.
CPC ............ *B01J 39/20* (2013.01); *B01D 15/361* (2013.01); *B01D 15/3804* (2013.01);
(Continued)

(58) Field of Classification Search
CPC . B01J 39/20; B01J 20/26; B01J 20/261; B01J 20/264; B01J 20/265; B01J 39/04;
(Continued)

(56) References Cited

U.S. PATENT DOCUMENTS

| 5,100,969 A | 3/1992 | Yamamoto |
| 6,780,322 B1 * | 8/2004 | Bissler .................... A61M 1/16 210/103 |

(Continued)

FOREIGN PATENT DOCUMENTS

| EP | 2009442 A2 | 12/2008 |
| JP | S49-029886 B | 3/1974 |

(Continued)

OTHER PUBLICATIONS

Akihiko Terada et al. "Bacterial adhesion to and viability on positively charged polymer surfaces." Microbiology 152 (2006), 3575-3583.

(Continued)

*Primary Examiner* — Joseph W Drodge
(74) *Attorney, Agent, or Firm* — Kratz, Quintos & Hanson, LLP

(57) ABSTRACT

The purpose of the present invention is to provide a method for separating and concentrating a target substance as an alternative to existing cationic polymers, and a kit for implementing this method.

5 Claims, 8 Drawing Sheets
(6 of 8 Drawing Sheet(s) Filed in Color)

(51) Int. Cl.
| | |
|---|---|
| *C12N 1/02* | (2006.01) |
| *C12N 1/20* | (2006.01) |
| *C08F 271/00* | (2006.01) |
| *C12N 7/00* | (2006.01) |
| *B01D 15/36* | (2006.01) |
| *B01D 15/38* | (2006.01) |
| *C12M 1/00* | (2006.01) |
| *B01J 20/26* | (2006.01) |
| *C12N 5/09* | (2010.01) |

(52) U.S. Cl.
CPC .......... *B01J 20/261* (2013.01); *B01J 20/264* (2013.01); *C08F 271/00* (2013.01); *C08F 283/00* (2013.01); *C12M 47/12* (2013.01); *C12N 1/02* (2013.01); *C12N 1/20* (2013.01); *C12N 5/0693* (2013.01); *C12N 7/00* (2013.01); *C12N 2795/00051* (2013.01)

(58) Field of Classification Search
CPC ......... B01J 39/16; B01J 39/26; C12N 5/0693; C12N 7/00; C12N 1/20; C12N 1/02; C12N 2795/00051; C12N 7/02; C08F 271/00; C08F 283/00; B01D 15/361; B01D 15/362; B01D 15/368; B01D 15/3804; B01D 15/3828; B01D 2015/3838; B01D 2221/10; C12M 47/02; C12M 47/04; C12M 47/12
USPC ................ 210/634, 635, 638, 656, 690–692; 422/430, 69, 70, 527; 435/5, 7.1, 287.7
See application file for complete search history.

(56) References Cited

U.S. PATENT DOCUMENTS

| | | | |
|---|---|---|---|
| 7,547,747 B2 | 6/2009 | Hashimoto | |
| 9,974,303 B2* | 5/2018 | Coady | A01N 37/44 |
| 2001/0009759 A1* | 7/2001 | Sato | C12N 7/00 435/5 |
| 2005/0269267 A1* | 12/2005 | Patton | C07K 1/26 210/656 |
| 2006/0073510 A1* | 4/2006 | Fox | G01N 33/54393 435/6.16 |
| 2006/0270031 A1* | 11/2006 | Hwang | C12N 1/02 435/325 |
| 2009/0001025 A1 | 1/2009 | Takahashi et al. | |
| 2010/0029544 A1 | 2/2010 | Cheng et al. | |
| 2010/0035757 A1* | 2/2010 | Furno | A61L 15/60 504/360 |
| 2012/0251602 A1* | 10/2012 | Doucet | A61K 8/44 424/401 |
| 2014/0301977 A1* | 10/2014 | Nadarajah | B01D 15/14 424/85.2 |
| 2015/0010848 A1 | 1/2015 | Suzuki | |
| 2015/0093800 A1* | 4/2015 | Mahajan | B01J 49/0078 435/188 |
| 2017/0008991 A1 | 1/2017 | Watanabe | |

FOREIGN PATENT DOCUMENTS

| | | |
|---|---|---|
| JP | S57-189692 A | 11/1982 |
| JP | H03-103478 A | 4/1991 |
| JP | H08-173194 A | 7/1996 |
| JP | 2002-125695 A | 5/2002 |
| JP | 2004-089787 A | 3/2004 |
| JP | 2004-225181 A | 8/2004 |
| JP | 2005-097636 A | 4/2005 |
| JP | 2005-154973 A | 6/2005 |
| JP | 2006-036830 A | 2/2006 |
| JP | 2007-159874 A | 6/2007 |
| JP | 2009-028711 A | 2/2009 |
| JP | 2009-235185 A | 10/2009 |
| JP | 2010-220581 A | 10/2010 |
| JP | 2011-024449 A | 2/2011 |
| JP | 2012-030222 A | 2/2012 |
| JP | 2013-231145 A | 11/2013 |
| WO | 2008107326 A1 | 9/2008 |
| WO | 2011120156 A1 | 10/2011 |
| WO | 2012/144554 A1 | 10/2012 |
| WO | 2013136762 A1 | 9/2013 |
| WO | 2015/146486 A1 | 10/2015 |

OTHER PUBLICATIONS

ISR for PCT/JP2015/055892.
Akihiko Kikuchi et al. "Effects of environmental parameters and composition of poly(2-hydroxyethyl methacrylate)-graft-polyamine copolymers on the retention of rat lymphocyte subpopulations (B- and T-cells)". J.Biomater. Sci. Polym. Ed., 1994, vol. 5, No. 6, pp. 569-590, with cover page. Cited in ISR.
Kataoka K., "Molecular design of cellular specific polymers and their application to cell separation technology".The Japanese Journal of Artificial Organs, 1991, vol. 20, No. 2, pp. 314 to 317. Cited in ISR. Translation of abstract.
Nittobo Medical Co., Ltd,"rapid BACpro; preparation kit for rapid identification of bacteria". Seminar: The Japan Society for Clinical Laboratory Automation(date of disclosure :Sep. 1, 2014). Seminor Text; Translation of abstract.
Ashizawa et al., Poster: "Investgiation of preparation method of direct detection for the purpose of bacterial identification with mass spectrometer". The Japan Society for Clinical Laboratory Automation (date of disclosure : Sep. 1, 2014).Translation of abstract.
Noda et al., "A novel preparation kit; rapid BACpro, for bacterial identification with matrix-assisted laser desorption ionization time-of-flight mass spectrometry". Japanese Society for Biomedical Mass Spectrometry(date of disclosure : Sep. 1, 2014) Translation of abstract.
Ashizawa et al., Poster: Development of a rapid microbial perparation system from a blood culture bottle using cationic particles for bacterial identification with matrix-assisted laser desorption ionization time-of-flight mass spectrometry. Human Proteome Organization(date of disclosure :Oct. 4, 2014). (Poster & Abstract).
ISR for related application PCT/JP2015/055891.
Written Opinion for corresponding PCT Application PCT/JP2015/055892; with translation.
Watanabe, K, U.S. Appl. No. 15/120,799, filed Aug. 23, 2016, corresponds to WO2015/146486.
Extended European Search Report for counterpart EPC Patent Application No. 15769422.5 dated Feb. 23, 2018 (11 Sheets).
Chinese Search Report for Chinese Application No. 2015800159805 dated Feb. 1, 2018 (2 Sheets).
Chinese Office Action for corresponding Chinese Patent Application No. 201580015980.5 dated Feb. 1, 2018 (4 Sheets, 5 Sheets translation, 9 Sheets total).
Extended European Search Report for corresponding EP application No. 15769789.7 dated Oct. 5, 2017 (6 Sheets).

* cited by examiner

LEFT : sup
RIGHT: pellet

1: NO TREATMENT WITH CATIONIC GRAFT POLYMER
2: TREATMENT WITH CATIONIC GRAFT POLYMER

FIG.5
(1) AGGREGATED STATE
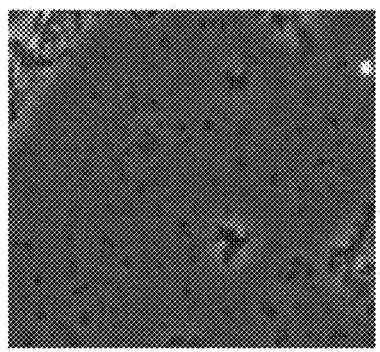
sup
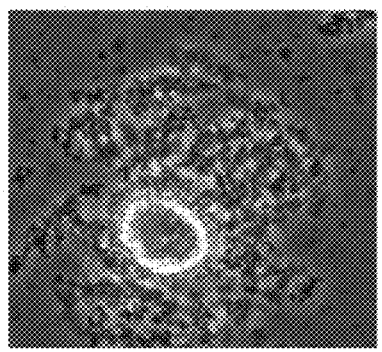
pellet
BLUE (DAPI): CELL (NUCLEUS)
BLACK: CATIONIC GRAFT POLYMER
(2) DISPERSED STATE
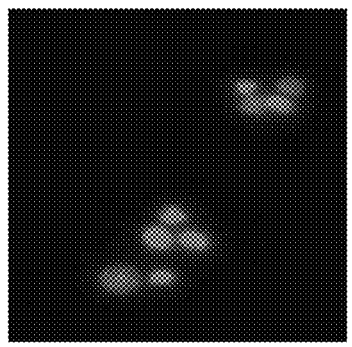
pellet
BLUE (DAPI): CELL (NUCLEUS)
FIG.6
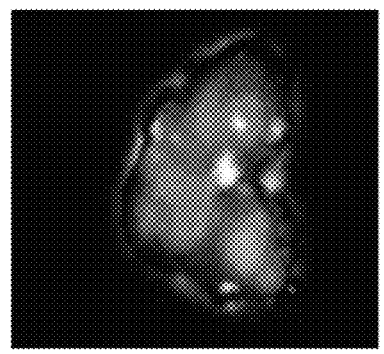
BLUE (DAPI): CELL (NUCLEUS)
GREEN (Alexa 488): ANTIBODY (MCAM)

FIG.7
(1) AGGREGATED STATE
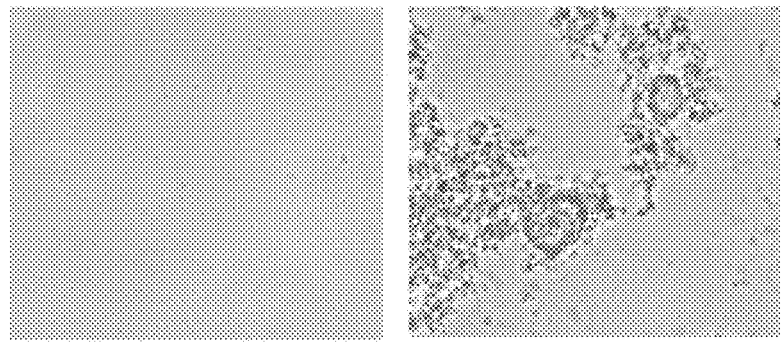
sup
pellet
BLACK: CATIONIC GRAFT POLYMER
GREEN (DyLight 488): VESICLE
(2) DISPERSED STATE
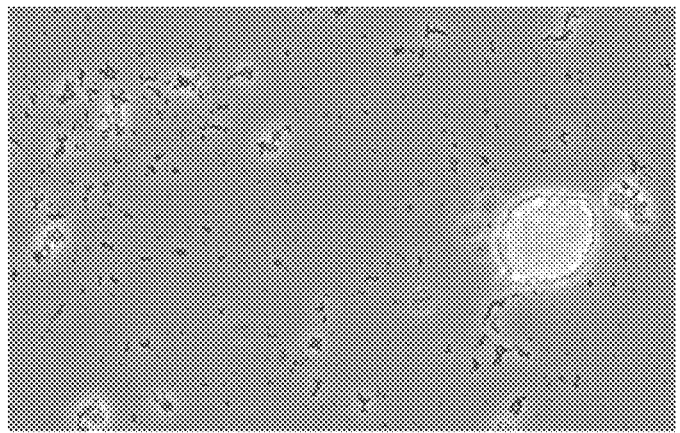
pellet
GREEN (DyLight 488): VESICLE
BLACK: CATIONIC GRAFT POLYMER GREEN (DyLight 488): VESICLE
RED (Alexa 594): ANTIBODY (MCAM)

LEFT: SAMPLE 2; RIGHT: SAMPLE 1

POSITIVE CONTROL     BACTERIOPHAGE COLLECTED
                     WITH GRAFT POLYMER

METHOD FOR SEPARATING AND CONCENTRATING TARGET SUBSTANCE USING NOVEL CATIONIC GRAFT POLYMER

TECHNICAL FIELD

The present application claims priority for Japanese Patent Applications No. 2014-60419 and No. 2014-60420 filed on Mar. 24, 2014, and the entire contents of the Japanese applications are incorporated herein by reference.

Description in all the literatures cited here and in the above two Japanese applications is incorporated herein.

The present invention relates to a target biomolecule separation and concentration method using a graft polymer which can be safely and stably produced with low introduction cost and a simple operation, and a kit used for the method.

BACKGROUND ART

An ion exchange polymer is a kind of synthetic resin, and has a structure for ionization as an ionic group in a part of the molecular structure thereof. The ion exchange polymer performs ion exchange with an ion in a solvent such as water. Behavior thereof is in accordance with selectivity for the ion. The ion exchange polymer is largely classified into a cation exchange polymer and an anion exchange polymer. By using a difference in adsorption between a fixed ion in the polymer and a counter ion (ion to be exchanged) in various solutions, ions contained in the solutions can be separated.

Electric charge characteristics of a biomolecule are determined by various factors such as a charge of the entire molecules, a charge density, a method of distribution of a surface charge, and the pH of a solution. For example, protein contains many kinds of ionic amino acids such weakly acidic and weakly basic amino acids, and has both a positive charge and a negative charge on surface of protein molecule. The sum of the charges is called an effective surface charge, and a charge state of an amino acid depends on the pH. Therefore, an effective surface charge of a protein molecule is changed into positive or negative charge, depending on the pH of a solution.

Ion exchange chromatography is a method of collecting a biomolecule based on reversible binding and eluting the biomolecule with a carrier having an opposite charge, by utilizing such a change of charge state (i.e., effective surface charge) of the biomolecule caused by the pH or a salt concentration (for example, Patent Literatures 1 and 2 and non-Patent Literature 1).

However, when such a collecting operation is performed, a surfactant, a high concentration salt, or the like is used during elution. Therefore, it is difficult to maintain a three-dimensional structure of a target or to collect the target while the target is alive.

CITATION LIST

Patent Literatures

PATENT LITERATURE 1: JP 1996-173194 A
PATENT LITERATURE 2: JP 2002-125695 A

Non-Patent Literature

Non-Patent Literature 1: Microbiology 152 (2006), 3575-3583

SUMMARY OF INVENTION

Technical Problem

An object of the present invention is to provide a method for separating and concentrating a target substance using a novel cationic graft polymer in place of an existing cationic polymer, and a kit therefor.

Solution to Problem

That is, the present invention is constituted by the following [1] to [11].

[1] A method for separating and concentrating a target substance using a cationic graft polymer, comprising:
(1) step of bringing the cationic graft polymer into contact with a sample containing the target substance to make the target substance bound to the cationic graft polymer under a basic condition;
(2) step of separating the bound complex of the cationic graft polymer and the target biomolecule; and
(3) step of eluting the target substance from the bound complex,
wherein the cationic graft polymer is a polyamine graft polymer obtained by polymerizing a polyamine derivative obtained by a reaction between (a) a polymer compound having at least one amino group and (b) a compound having at least one epoxy group, and (c) an ethylenically unsaturated monomer;

[2] the method according to the above [1], further comprising adding a divalent or trivalent metal ion in step (1);

[3] the method according to the above [1] or [2], further comprising a step for washing the bound complex in step (2); and

[4] the method according to any one of the above [1] to [3], wherein the cationic graft polymer is fixed to a solid phase surface.

[5] The method according to any one of the above [1] to [3], comprising a step for aggregating a cationic graft polymer which is not bound to the target substance in step (3).

[6] A kit used for the method according to any one of the above [1] to [5], comprising a cationic graft polymer;

[7] the kit according to the above [6], further comprising a metal ion salt;

[8] the kit according to the above [6], further comprising a reaction solution containing a basic solution and a divalent or trivalent metal ion salt;

[9] the kit according to any one of the above [6] to [8], further comprising a washing solution; and

[10] the kit according to any one of the above [6] to [9], further comprising a dispersion solution containing an acidic solution or a chelating agent.

[11] The kit according to any one of the above [6] to [10], further comprising an aggregation solution.

Advantageous Effects of Invention

The method of the present invention allows a target substance in a sample to be separated and concentrated efficiently, and the target substance is less damaged than a known method in a process of separation and concentration, and therefore is easily analyzed thereafter. More specifically, the method of the present invention can be applied to analysis using a mass spectroscope.

BRIEF DESCRIPTION OF DRAWINGS

The patent or application file contains at least one drawing executed in color. Copies of this patent or patent application publication with color drawing(s) will be provided by the Office upon request and payment of the necessary fee.

*Escherichia coli* is absent in the left tube, and *Escherichia coli* is present in the right tube.

Figure 2:
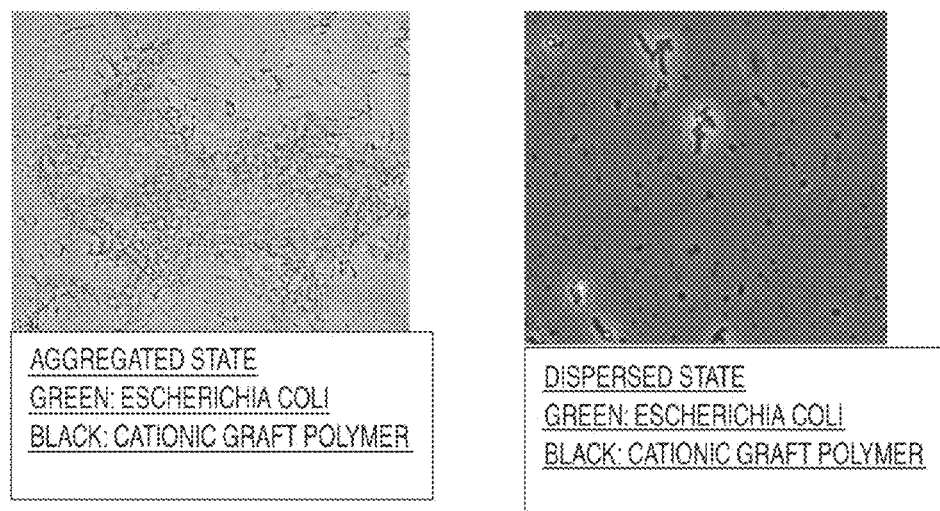

FIG. 2 Fluorescence microscopic observation of bound complex of GFP-expressing *Escherichia coli* and cationic graft polymer GFP expressed by *Escherichia coli* was detected with a laser wavelength (488 nm). The cationic graft polymer and *Escherichia coli* were detected with visible light. Images were continuously acquired with a laser wavelength and visible light, and were superimposed by a pseudo-color display. The left drawing illustrates a state in which *Escherichia coli* is captured by the cationic graft polymer. The right drawing illustrates a state in which the pellet is dispersed with a dispersion solution.

Figure 3:
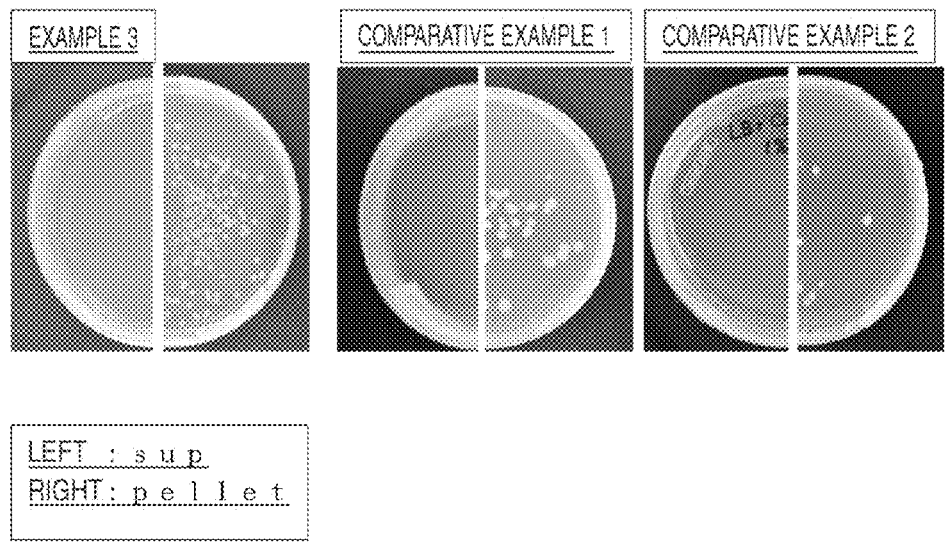

FIG. 3 Confirmation of survival (Viability) of separated *Escherichia coli*

A cationic graft polymer was allowed to react with *Escherichia coli*. Each of a supernatant after centrifugation and a solution in which a pellet was dispersed with a dispersion solution was cultured. The right image indicates the supernatant, and the left image indicates the dispersion solution.

Figure 4:
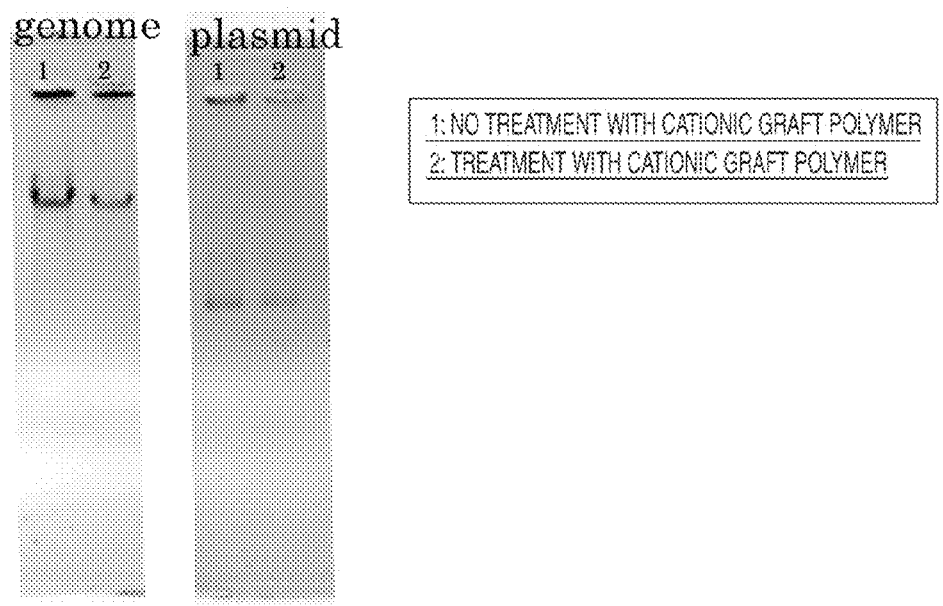

FIG. 4 Electrophoresis using separated and collected nucleic acid

Lane 1 indicates an electrophoresis image of a sample not treated with a cationic graft polymer, and lane 2 indicates an electrophoresis image of a sample treated with the cationic graft polymer.

FIG. 5 Detection of collected cell (1) Supernatant (left) and pellet (right) after reaction between cell and cationic graft polymer and centrifugation (2) State in which the pellet is dispersed with dispersion solution In both (1) and (2), a nucleus of the cell was detected with a laser wavelength of 350 nm, and the cationic graft polymer was detected with visible light. Images were continuously acquired with a laser wavelength and visible light. The images were superimposed by a pseudo-color display, and an aggregation state and a dispersion state were observed.

FIG. 6 Fluorescence microscopic observation of collected cell

A cell was captured by a cationic graft polymer, and was dispersed with a dispersion solution. Thereafter, immunostaining was performed. A nucleus of the cell was detected with a laser wavelength of 350 nm, and an antibody to react with an antigen (MCAM) expressed on a surface of the cell was detected with 488 nm Images were continuously acquired with two kinds of laser wavelengths. The images were superimposed by a pseudo-color display, and the antigen on a surface of the cell was observed.

FIG. 7 Detection of collected vesicle (1) Supernatant (left) and pellet (right) after reaction between vesicle and cationic graft polymer and centrifugation (2) State in which the pellet is dispersed with dispersion solution In both (1) and (2), a vesicle was detected with a laser wavelength of 488 nm, and the cationic graft polymer was detected with visible light. Images were continuously acquired with a laser wavelength and visible light. The images were superimposed by a pseudo-color display, and an aggregation state and a dispersion state were confirmed.

Figure 8:
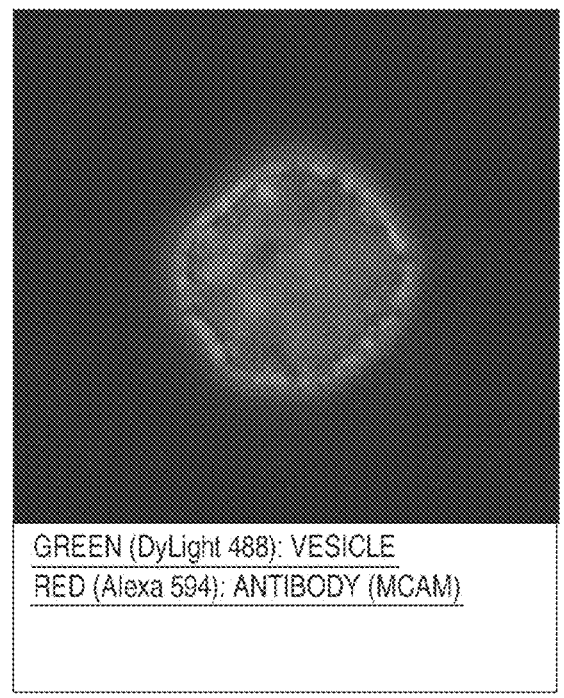

FIG. 8 Fluorescence microscopic observation of collected vesicle

A vesicle captured by a cationic graft polymer was dispersed with a dispersion solution, and then immunostaining was performed.

The vesicle was detected with a laser wavelength of 488 nm, and an antibody was detected with a laser wavelength of 594 nm Images were continuously acquired with two kinds of laser wavelengths. The images were superimposed by a pseudo-color display, and a state of the antigen on a surface of the vesicle was confirmed.

Figure 9:
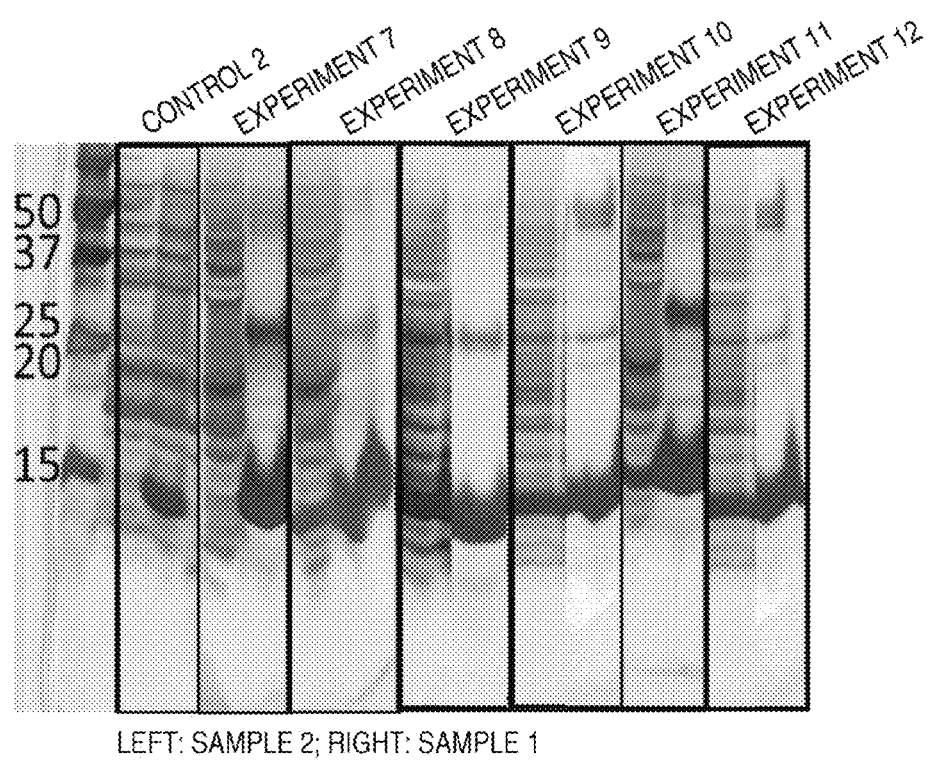

FIG. 9 Detection of *Escherichia coli* collected using surfactant-containing solution (electrophoresis)

Figure 10:
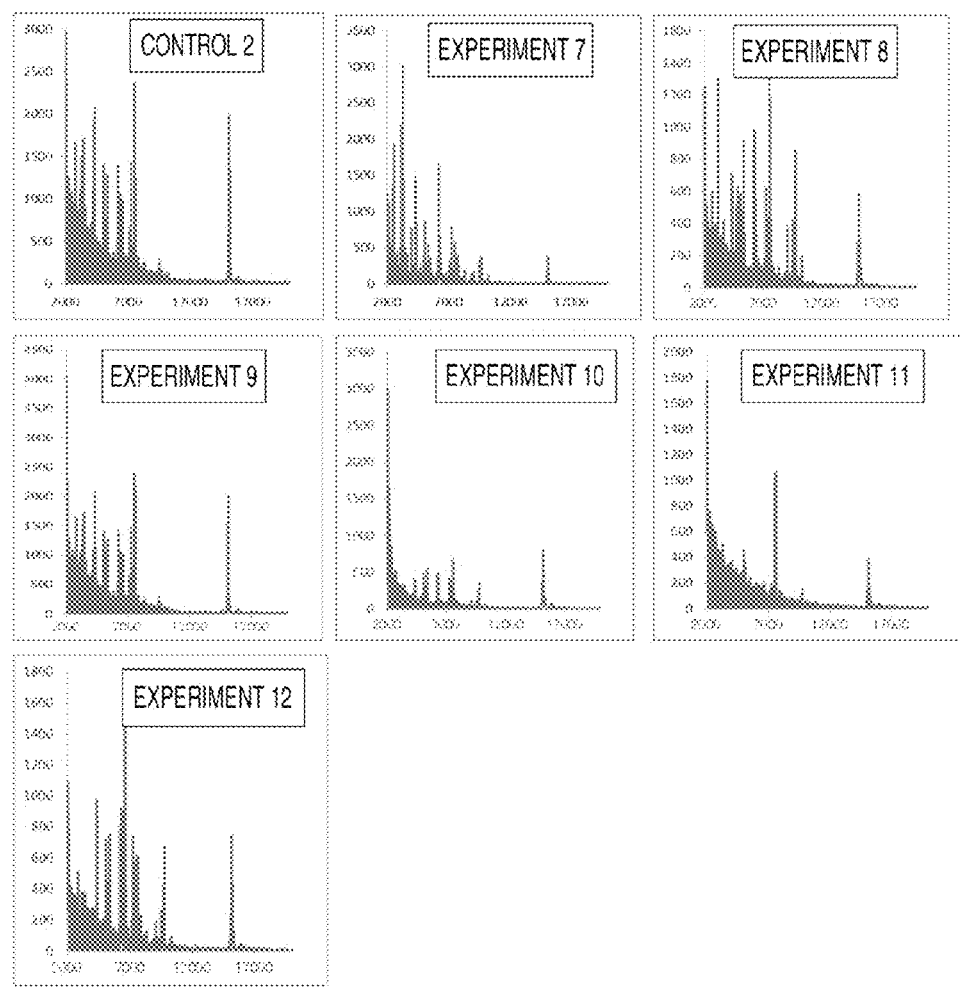

FIG. 10 Detection of *Escherichia coli* collected using surfactant-containing solution (mass spectrometry)

Figure 11:
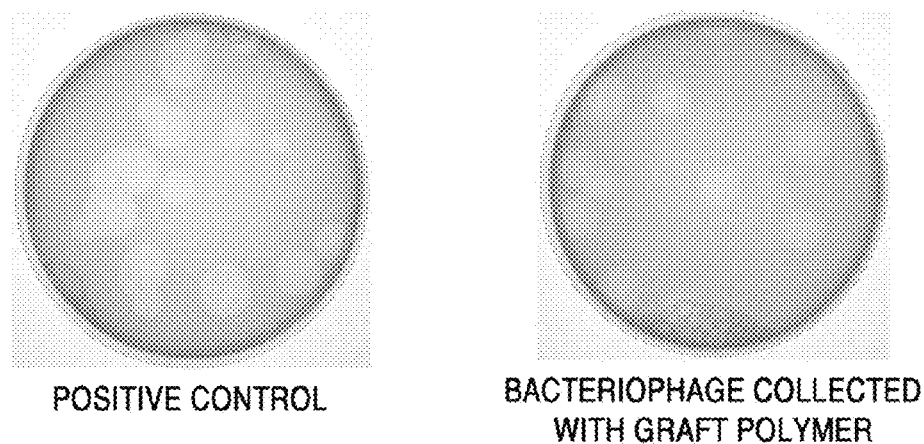

FIG. 11 Separation and detection of bacteriophage

Figure 12:
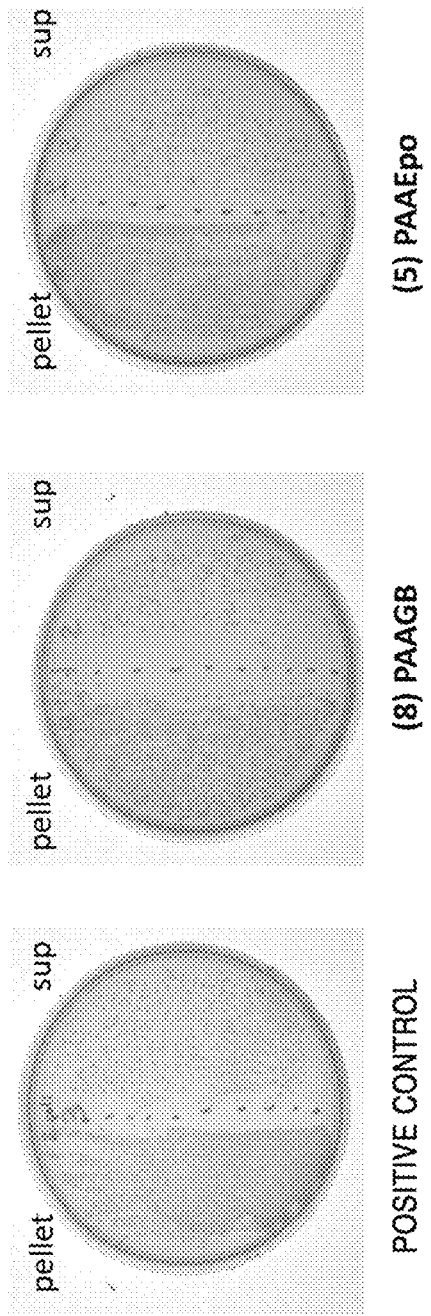

FIG. 12 Confirmation of survival of separated *Escherichia coli*

*Escherichia coli* was separated using a graft polymer of epoxy octane-modified polyallylamine and diallyl dimethyl ammonium chloride (PAAEpo-g-DADMAC) and a graft polymer of glycidyl butyrate-modified polyallylamine and diallyl dimethyl ammonium chloride (PAAGB-g-DADMAC). Each of the graft polymers was mixed with latex beads, and then was allowed to react with a bacterial cell.

Figure 13:
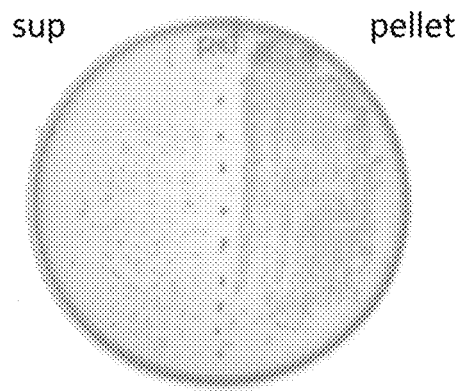

FIG. 13 Confirmation of survival of separated *Escherichia coli*

*Escherichia coli* was separated using a graft polymer of epoxy octane-modified polyallylamine and diallyl dimethyl ammonium chloride (PAAEpo-g-DADMAC). The graft polymer was allowed to react with a bacterial cell, and then latex beads were added thereto.

Figure 14:
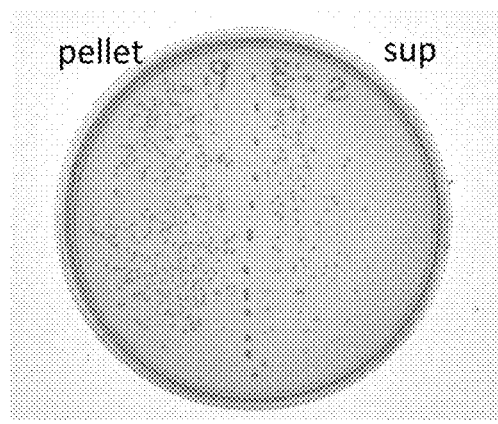

FIG. 14 Confirmation of survival of separated *Escherichia coli*

*Escherichia coli* was separated using a graft polymer of glycidol-modified polydiallylamine and diallyl dimethyl ammonium chloride (DAAGly-g-DADMAC). Each of the graft polymers was mixed with latex beads, and then was allowed to react with a bacterial cell.

Figure 15:
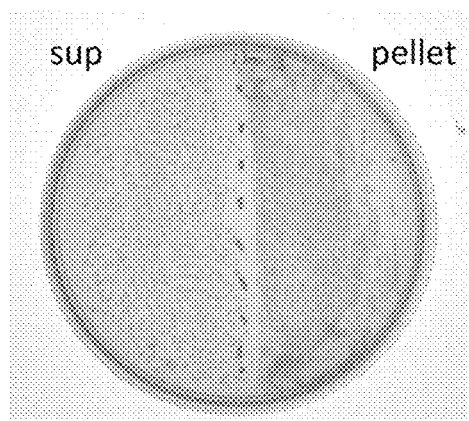

FIG. 15 Confirmation of survival of separated *Escherichia coli*

*Escherichia coli* was separated using a graft polymer of glycidol-modified polydiallylamine and diallyl dimethyl ammonium chloride (DAAGly-g-DADMAC). The graft polymer was allowed to react with a bacterial cell, and then latex beads were added thereto.

DESCRIPTION OF EMBODIMENTS

A "cationic graft polymer" is obtained by polymerizing a polyamine derivative obtained by a reaction between (a) a polymer compound having at least one amino group and (b) a compound having at least one epoxy group, and (c) an ethylenically unsaturated monomer [the polymer compound having at least one amino group (a) may be selected from the group consisting of an ethyleneimine polymer represented by general formula (1), a vinylamine polymer represented by general formula (2), an allylamine polymer represented by general formula (3), a diallylamine polymer represented by general formula (4), and an acrylic amine polymer represented by general formula (5) (in the following general formulae, n is an integer of from 10 to 200,000, m is an integer of from 5 to 3,000, l is an integer of from 5 to 5,000, o is an integer of from 10 to 10,000, and p is an integer of from 1 to 100)].

[FORMULA 1]

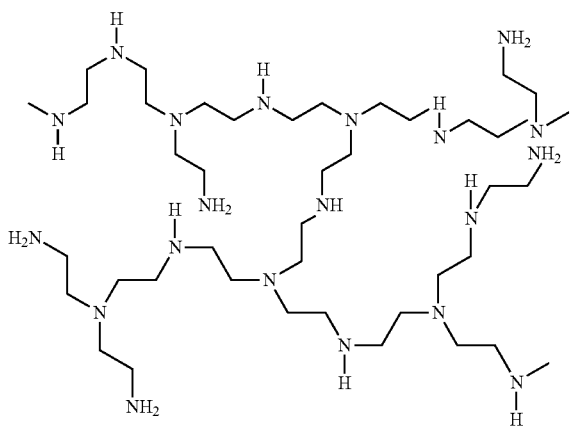

(1)

[FORMULA 2]

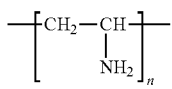

(2)

[FORMULA 3]

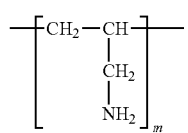

(3)

[FORMULA 4]

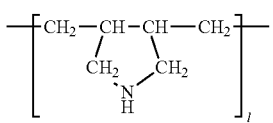

(4)

[FORMULA 5]

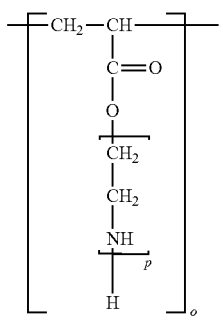

(5)

The "polymer compound having at least one amino group (a)" is only required to have at least one amino group, and may contain a constituent unit having no amino group in constituent units thereof. Therefore, each of polymers having the structures represented by the above general formulae (1) to (5) may contain a constituent unit having no amino group in addition to each of the constituent units of the structures represented by the above general formulae (1) to (5), or does not have to contain the constituent unit having no amino group. Examples of the constituent unit having no amino group include sulfur dioxide, acrylamide, allyl alcohol, and acrylic acid. However, the constituent unit having no amino group is not limited thereto.

The "amino group" in the "polymer compound having at least one amino group (a)" may be a primary amino group, a secondary amino group, or a tertiary amino group, and is particularly preferably a primary amino group or a secondary amino group.

The number of the "amino group" in the "polymer compound having at least one amino group (a)" is not particularly limited, but is preferably form 5 to 15000, and particularly preferably from 8 to 3000 per polymer from a viewpoint of reactivity, usability, or the like. In terms of the number per molecular weight of the polymer compound, the number is preferably from 5 to 230, and particularly preferably from 10 to 130 per molecular weight 10000.

The molecular weight of the "polymer compound having at least one amino group (a)" is not particularly limited, but is preferably from 500 to 10000000, and particularly preferably from 500 to 1000000 in terms of a number average molecular weight from a viewpoint of reactivity, viscosity, handling, yield, or the like.

The numbers of repeating units of the polymer compound having at least one amino group (a) used in the first invention of the present application is not particularly limited, but is preferably form 10 to 150000, and particularly preferably from 10 to 3000 from a viewpoint of reactivity, viscosity, handling, yield, or the like.

The "polymer compound having at least one amino group (a)" may be an "allylamine monomer further having at least one allyl group and at least one amino group (a')". Any polymerizable compound having at least one allyl group and at least one amino group in a structure thereof can be used, but an allylamine compound having a structure represented by general formula (a1) is preferable.

[FORMULA 6]

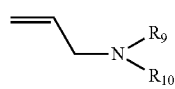

-(a1)

In general formula (a1), at least one of $R_9$ and $R_{10}$ is a hydrogen atom, and the other is a hydrogen atom or a hydrocarbon group having 1 to 8 carbon atoms, and is preferably a hydrogen atom or an alkyl group having 1 to 3 carbon atoms.

It is particularly preferable from a viewpoint of polymerizability or the like that one of $R_9$ and $R_{10}$ is also an allyl group in general formula (a1), that is, the allylamine monomer (a') is a diallylamine monomer having two allyl groups.

It is preferable that at least a part of allylamine monomer (a') is a diallylamine monomer having two allyl groups from a viewpoint of obtaining high polymerizability. It is more preferable that 30 mol % or more of the allylamine monomer (a') is a diallylamine monomer. It is particularly preferable that 50 mol % or more of the allylamine monomer (a') is a diallylamine monomer.

In general formula (a1), when one of $R_9$ and $R_{10}$ (for example, $R_9$) is a hydrogen atom, the other (in this case, $R_{10}$)

is preferably a hydrogen atom, a methyl group, an ethyl group, an allyl group, or a benzyl group. That is, the allylamine compound having a structure represented by general formula (a1) is preferably allylamine, methyl allylamine, ethyl allylamine, diallylamine, or benzyl allylamine An organic acid salt or an inorganic acid salt of the allylamine compound having a structure represented by general formula (a1) also can be preferably used as the allylamine monomer having at least one allyl group and at least one amino group (a') in the first invention of the present application. As a counter ion in the organic acid salt or the inorganic acid salt, a halogen ion (more preferably, $Cl^-$, $Br^-$, or $I^-$), a methyl sulfate ion, an ethyl sulfate ion, a methanesulfonate ion, a 2-hydroxy-1-ethanesulfonate ion, an acetate ion, or a hydroxy acetate ion is preferable.

In the above definition, the cationic graft polymer may be a polyamine graft polymer in which the "compound having at least one epoxy group (b)" is a compound represented by general formula (6) (R in general formula (6) is a substituted or unsubstituted monovalent hydrocarbon group).

[FORMULA 7]

-(6)

In the above definition, the cationic graft polymer may be a polyamine graft polymer in which the "compound having at least one epoxy group (b)" is a compound represented by general formula (7), selected from the group consisting of (1) ethylene oxide in which $R_1$, $R_2$, $R_3$, and $R_4$ in the formula are each a hydrogen atom in the formula, (2) an epoxy compound in which $R_1$, $R_2$, $R_3$, and $R_4$ in the formula are each independently a hydrogen atom or a linear or branched saturated hydrocarbon group having a hydroxy group in a chain and having 1 to 8 carbon atoms (not all of $R_1$, $R_2$, $R_3$, and $R_4$ in the formula are hydrogen atoms), (3) an epoxy compound in which $R_1$, $R_2$, $R_3$, and $R_4$ in the formula are each independently a hydrogen atom or a substituted or unsubstituted monovalent hydrocarbon group (not all of $R_1$, $R_2$, $R_3$, and $R_4$ in the formula are hydrogen atoms), (4) an epoxy compound in which $R_1$, $R_2$, $R_3$, and $R_4$ in the formula are each independently a hydrogen atom or a linear or branched saturated hydrocarbon group having an ether bond in a chain and having 1 to 8 carbon atoms (not all of $R_1$, $R_2$, $R_3$, and $R_4$ are hydrogen atoms), (5) an epoxy compound in which $R_1$, $R_2$, $R_3$, and $R_4$ in the formula are each independently a hydrogen atom or a halogen atom (not all of $R_1$, $R_2$, $R_3$, and $R_4$ are not hydrogen atoms), (6) an epoxy compound in which $R_1$, $R_2$, $R_3$, and $R_4$ in the formula are each independently a hydrogen atom or an unsaturated hydrocarbon group (not all of $R_1$, $R_2$, $R_3$, and $R_4$ are hydrogen atoms), (7) an epoxy compound in which $R_1$, $R_2$, $R_3$, and $R_4$ in the formula are each independently a hydrogen atom or a hydrocarbon group containing an alicyclic hydrocarbon group or a cyclic hydrocarbon group having an unsaturated bond (not all of $R_1$, $R_2$, $R_3$, and $R_4$ are hydrogen atoms), (8) an epoxy compound in which $R_1$, $R_2$, $R_3$, and $R_4$ in the formula are each independently a hydrogen atom or a hydrocarbon group containing an aromatic ring or a heterocyclic ring (not all of $R_1$, $R_2$, $R_3$, and $R_4$ are hydrogen atoms), (9) a polyfunctional epoxy compound in which $R_1$, $R_2$, $R_3$, and $R_4$ in the formula are each independently a hydrogen atom or a hydrocarbon group containing an epoxy ring (not all of $R_1$, $R_2$, $R_3$, and $R_4$ are hydrogen atoms), (10) an epoxy compound in which $R_1$, $R_2$, $R_3$, and $R_4$ in the formula are each independently a hydrogen atom or a linear or branched saturated hydrocarbon group containing an alkoxysilyl in a chain and having 3 to 12 carbon atoms (not all of $R_1$, $R_2$, $R_3$, and $R_4$ are hydrogen atoms), (11) an epoxy compound in which $R_1$, $R_2$, $R_3$, and $R_4$ in the formula are each independently a hydrogen atom or a hydrocarbon group containing a fluorine atom in a chain (not all of $R_1$, $R_2$, $R_3$, and $R_4$ are hydrogen atoms), (12) an epoxy compound in which $R_1$, $R_2$, $R_3$, and $R_4$ in the formula are each independently a hydrogen atom or a hydrocarbon group containing a carboxyl group in a chain (not all of $R_1$, $R_2$, $R_3$, and $R_4$ are hydrogen atoms), (13) an epoxy compound in which $R_1$, $R_2$, $R_3$, and $R_4$ in the formula are each independently a hydrogen atom or a linear or branched saturated hydrocarbon group containing an ester bond or an amide bond in a chain and having 1 to 12 carbon atoms (not all of $R_1$, $R_2$, $R_3$, and $R_4$ are hydrogen atoms), and (14) an epoxy compound in which $R_1$, $R_2$, $R_3$, and $R_4$ in the formula are each independently a hydrogen atom or a hydrocarbon group containing a sulfonate group in a chain (not all of $R_1$, $R_2$, $R_3$, and $R_4$ are hydrogen atoms).

[FORMULA 8]

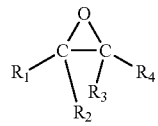

(7)

Examples of the "compound having at least one epoxy group (b)" include ethylene oxide (refer to the following formula for a structure thereof),

[FORMULA 9]

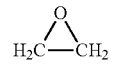

glycidol (refer to the following formula for a structure thereof),

[FORMULA 10]

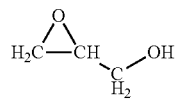

propylene oxide (refer to the following formula for a structure thereof),

[FORMULA 11]

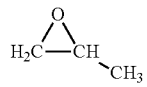

butylene oxide, 2,3-butylene oxide, 1,2-epoxy hexane, and 1,2-epoxy hexadecane, glycidyl methyl ether (refer to the following formula for a structure thereof),

[FORMULA 12]

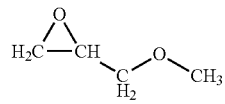

ethyl glycidyl ether, glycidyl isopropyl ether, and triglycidyl isocyanurate,
epichlorohydrin (refer to the following formula for a structure thereof),

[FORMULA 13]

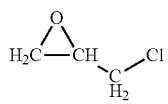

epibromohydrin and 2-(chloromethyl)-1,2-epoxy butane,
1,3-butadiene monoxide (refer to the following formula for a structure thereof),

[FORMULA 14]

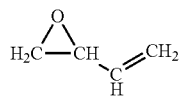

1,2-epoxy-5-hexene and allyl glycidyl ether,
1,2-epoxy cyclopentane (refer to the following formula for a structure thereof),

[FORMULA 15]

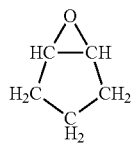

1,2-epoxy cyclohexane and 1,2-epoxy-4-vinyl cyclohexane
3,4-epoxy tetrahydrofuran,
styrene oxide (refer to the following formula for a structure thereof),

[FORMULA 16]

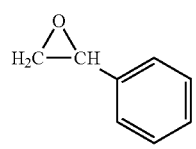

glycidyl phenyl ether and 4-glycidyloxy carbazole,
1,2:3,4-diepoxy butane (refer to the following formula for a structure thereof),

[FORMULA 17]

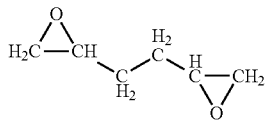

1,4-butanediol diglycidyl ether and ethylene glycol diglycidyl ether,
3-glycidoxypropyl trimethoxysilane (refer to the following formula for a structure thereof),

[FORMULA 18]

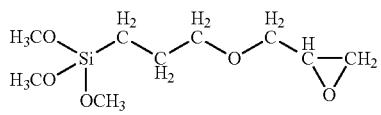

and 3-glycidyloxypropyl (dimethoxy) methylsilane,
1,2-epoxy-1H, 1H, 2H, 3H, 3H heptadecafluoro undecane (refer to the following formula for a structure thereof),

[FORMULA 19]

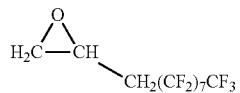

epoxy succinic acid (refer to the following formula for a structure thereof),

[FORMULA 20]

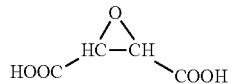

glycidyl butyrate (refer to the following formula for a structure thereof),

[FORMULA 21]

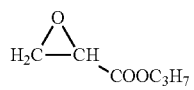

and N-glycidylphthalimide, and
glycidyl nitrobenzesulfonate (refer to the following formula for a structure thereof),

[FORMULA 22]

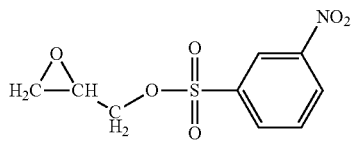

and glycidyl-p-toluenesulfonate. However, the compound (b) having at least one epoxy group is not limited thereto.

In the above definition, the cationic graft polymer may be a polyamine graft polymer in which the "ethylenically unsaturated monomer (c)" is selected from the group consisting of a vinyl monomer, a styrene monomer, a methacrylate monomer, an acrylate monomer, an acrylamide monomer, an allyl monomer, a diallyl monomer, and an unsaturated carboxylic acid.

The molecular weight of the ethylenically unsaturated monomer (c) is not particularly limited, but is preferably from 28 to 1100, and particularly preferably from 28 to 500 from a viewpoint of a graft efficiency or the like.

The number of carbon atoms in the ethylenically unsaturated monomer (c) is not particularly limited, but is preferably from 2 to 50, and particularly preferably from 2 to 30.

More specific examples of the ethylenically unsaturated monomer (c) preferably used in the present invention include styrene, divinylbenzene, sodium p-styrenesulfonate hydrate, vinylbenzyl trimethyl ammonium chloride, vinyl acetate, 1-vinylimidazole, 2-vinylpyridine, acrylonitrile, allylamine hydrochloride, diallylamine hydrochloride, dimethyl diamine hydrochloride, diallyl dimethyl ammonium chloride, particularly a 60% aqueous solution thereof, dimethyl acrylamide, hydroxyethyl acrylamide, dimethylaminopropyl acrylamide, dimethylaminopropyl acrylamide methyl chloride quaternary salt, N-(3-dimethylaminopropyl) methacrylamide, 3-(trimethoxysilyl) propyl methacrylate, methyl acrylate, and butyl acrylate. Among these monomers, dimethyl acrylamide, diallyl dimethyl ammonium chloride, styrene, acrylonitrile, and the like are particularly preferable from a viewpoint of reactivity with a carbon atom adjacent to a hydroxy group on the trunk polymer, usefulness of a group at a terminal of a side chain after grafting, or the like.

The chemical structure, the CAS number, or the like of each of these monomers is obvious to a person skilled in the art, and therefore description thereof will be omitted.

The ethylenically unsaturated monomer (c) can be used singly or in combination of two or more kinds thereof according to a purpose of the present invention. When the ethylenically unsaturated monomer (c) is used in combination of two or more kinds thereof, all of the monomers may correspond to the above preferable examples, or only some monomers may correspond to the above preferable examples.

The amount of an amino group per unit weight contained in the cationic graft polymer is preferably from 0.1 to 17 mmol/g, and particularly preferably from 1 to 10 mmol/g. When the cationic graft polymer is not fixed to a solid phase surface, the average particle diameter is preferably 250 nm or less, and more preferably from 100 nm to 200 nm.

As forms of the "cationic graft polymer", the following graft polymers are exemplified.

(1) Graft Polymer of Propylene Oxide-Modified Polyallylamine and Dimethyl Acrylamide Propylene oxide (2 equivalents with respect to amine) was dropwise added to 20% by mass polyallylamine (weight average molecular weight: 3000) while the polyallylamine was cooled with ice water and was stirred. After a reaction at 20° C. for 24 hours, the solution was concentrated to obtain propylene oxide-modified polyallylamine as an aqueous solution.

Water was added to 42% by mass propylene oxide-modified polyallylamine prepared according to the above method such that the concentration became 14% by mass, and the resulting solution was stirred at 20° C. The reaction solution had a pH of 10. Subsequently, each of 65% by mass dimethylacrylamide (3 equivalents with respect to amine) and 12.01 g of 28.5% by mass APS aqueous solution (10 mol % with respect to monomer) was added thereto dividedly, and polymerization was performed for 24 hours to obtain a graft polymer of propylene oxide-modified polyallylamine and dimethyl acrylamide as an aqueous solution (weight average molecular weight: 120000).

(2) Graft Polymer of Propylene Oxide-Modified Polyallylamine and Diallyl Dimethyl Ammonium Chloride Water was added to 50% by mass propylene oxide-modified polyallylamine prepared in a similar manner to (1) such that the concentration became 30% by mass, and the resulting solution was stirred at 20° C. The reaction solution had a pH of 10. Subsequently, 65% by mass diallyl dimethyl ammonium chloride (3 equivalents with respect to amine) was added thereto. In addition, 96.08 g of 28.5% by mass APS aqueous solution (20 mol % with respect to monomer) was added thereto dividedly, and polymerization was performed for 72 hours to obtain a graft polymer of propylene oxide-modified polyallylamine and diallyl dimethyl ammonium chloride as an aqueous solution (weight average molecular weight: 24000).

(3) Graft Polymer of Propylene Oxide-Modified Polyallylamine and Styrene

Propylene oxide (0.1 equivalents with respect to amine) was dropwise added to 20% by mass polyallylamine while the polyallylamine was cooled with ice water and was stirred. After a reaction at 20° C. for 24 hours, the solution was concentrated to obtain propylene oxide-modified polyallylamine as an aqueous solution.

Water was added to the propylene oxide-modified polyallylamine such that the concentration became 20% by mass, then styrene (0.3 equivalents with respect to amine) was added thereto, and the resulting solution was stirred at 20° C. The reaction solution had a pH of 12. Thereafter, 12.01 g of 28.5% by mass APS aqueous solution (20 mol % with respect to monomer) was added thereto, and polymerization was performed for 24 hours. Thereafter, the resulting solution was heated at 70° C. for 24 hours to obtain a graft polymer of propylene oxide-modified polyallylamine and styrene having the following structure estimated (in the following general formula, q is an integer of from 0 to 3,000, r is an integer of from 0 to 3,000, s is an integer of from 0 to 3,000, t is an integer of from 0 to 10,000, u is an integer of from 0 to 10,000, and w is an integer of from 0 to 10,000). The graft polymer had an average particle diameter of 120 nm

[FORMULA 23]

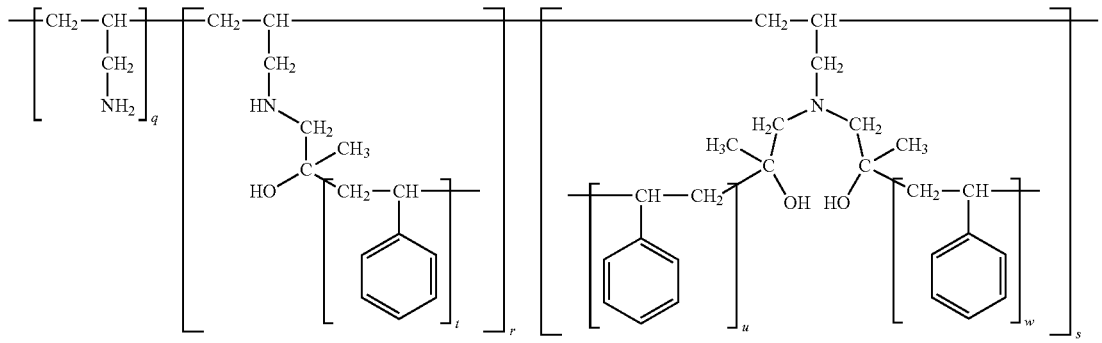

(4) Production of Graft Polymer of Propylene Oxide-Modified Polyallylamine and Dimethyl Acrylamide (Production at pH of 7)

Water was added to 42% by mass propylene oxide-modified polyallylamine prepared in a similar manner to (1) such that the concentration became 14% by mass, and the resulting solution was stirred at 20° C. Subsequently, 35% by mass hydrochloric acid was added thereto to adjust the pH to 7. Each of dimethyl acrylamide (3 equivalents with respect to amine) and 12.01 g of 28.5% by mass APS aqueous solution (10 mol % with respect to monomer) was added thereto dividedly, and polymerization was performed for 24 hours to obtain a graft polymer of propylene oxide-modified polyallylamine and dimethyl acrylamide as an aqueous solution (weight average molecular weight: 210000).

(5) Graft Polymer of Epoxy Octane-Modified Polyallylamine and Diallyl Dimethyl Ammonium Chloride Water was added to 20% by mass polyallylamine such that the concentration became 13% by mass, and epoxy octane (0.1 equivalents with respect to amine) was dropwise added thereto while the solution was cooled with ice water and was stirred. After dropwise addition, the solution was allowed to react at 40° C. for 24 hours, and then was concentrated to obtain epoxy octane-modified polyallylamine as an aqueous solution.

Water was added to 30% by mass epoxy octane-modified polyallylamine prepared according to the above method such that the concentration became 19% by mass, and the resulting solution was stirred at 20° C. The reaction solution had a pH of 12. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly to obtain a graft polymer of epoxy octane-modified polyallylamine and diallyl dimethyl ammonium chloride as an aqueous solution.

(6) Graft Polymer of Ethylene Glycol Diglycidyl Ether Modified Polyallylamine and Diallyl Dimethyl Ammonium Chloride Water was added to 20% by mass polyallylamine such that the concentration became 13% by mass, and ethylene glycol diglycidyl ether (0.05 equivalents with respect to amine) was dropwise added thereto while the solution was cooled with ice water and was stirred. After dropwise addition, the solution was allowed to react at 40° C. for 24 hours, and then was concentrated to obtain ethylene glycol diglycidyl ether modified polyallylamine as an aqueous solution.

Water was added to 30% by mass ethylene glycol diglycidyl ether modified polyallylamine prepared according to the above method such that the concentration became 19% by mass, and the resulting solution was stirred at 20° C. The reaction solution had a pH of 12. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours to obtain a graft polymer of ethylene glycol diglycidyl ether modified polyallylamine and diallyl dimethyl ammonium chloride as a yellow gel.

(7) Graft Polymer of Styrene Oxide-Modified Polyallylamine and Diallyl Dimethyl Ammonium Chloride Water was added to 20% by mass polyallylamine such that the concentration became 13% by mass, and styrene oxide (0.1 equivalents with respect to amine) was dropwise added thereto while the solution was cooled with ice water and was stirred. After dropwise addition, the solution was allowed to react at 40° C. for 24 hours, and then was concentrated to obtain styrene oxide-modified polyallylamine as an aqueous solution.

Water was added to 30% by mass styrene oxide-modified polyallylamine prepared according to the above method such that the concentration became 19% by mass, and the resulting solution was stirred at 20° C. The reaction solution had a pH of 12. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly to obtain a graft polymer of styrene oxide-modified polyallylamine and diallyl dimethyl ammonium chloride as an aqueous solution.

(8) Graft Polymer of Glycidyl Butyrate-Modified Polyallylamine and Diallyl Dimethyl Ammonium Chloride Water was added to 20% by mass polyallylamine such that the concentration became 13% by mass, and glycidyl butyrate (0.1 equivalents with respect to amine) was dropwise added thereto while the solution was cooled with ice water and was stirred. After dropwise addition, the solution was allowed to react at 40° C. for 24 hours, and then was concentrated to obtain glycidyl butyrate-modified polyallylamine as an aqueous solution.

Water was added to 30% by mass glycidyl butyrate-modified polyallylamine prepared according to the above method such that the concentration became 19% by mass, and the resulting solution was stirred at 20° C. The reaction solution had a pH of 12. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly to obtain a graft polymer of glycidyl butyrate-modified polyallylamine and diallyl dimethyl ammonium chloride as an aqueous solution.

(9) Graft Polymer of Propylene Oxide-Modified Polyallylamine and Styrene

Water was added to the propylene oxide-modified polyallylamine prepared in a similar manner to (3) such that the concentration became 20% by mass, then styrene (0.3 equivalents with respect to amine) was added thereto, and the resulting solution was stirred at 20° C. The reaction solution had a pH of 12. Thereafter, 12.53 g of 28.5% by mass SPS aqueous solution (20 mol % with respect to monomer) was added thereto, and polymerization was performed for 24 hours. Thereafter, the resulting solution was heated at 70° C. for 24 hours to obtain a graft polymer of propylene oxide-modified polyallylamine and styrene. The graft polymer had an average particle diameter of 135 nm.

(10) Graft Polymer of Propylene Oxide-Modified Polyallylamine and Styrene

Water was added to the propylene oxide-modified polyallylamine prepared in a similar manner to (3) such that the concentration became 20% by mass, then styrene (0.3 equivalents with respect to amine) was added thereto, and the resulting solution was stirred at 80° C. The reaction solution had a pH of 12. Thereafter, 12.01 g of 28.5% by mass APS aqueous solution (20 mol % with respect to monomer) was dropwise added thereto, and polymerization was performed for 24 hours to obtain a graft polymer of propylene oxide-modified polyallylamine and styrene. The graft polymer had an average particle diameter of 144 nm.

(11) Graft Polymer of Glycidol-Modified Polydiallylamine and Diallyl Dimethyl Ammonium Chloride Water was added to diallylamine such that the concentration became 79% by mass, and glycidol (1 equivalent with respect to amine) was dropwise added thereto while the solution was cooled with ice water and was stirred. After dropwise addition, the solution was allowed to react at 45° C. for 24 hours, and then was concentrated to obtain glycidol-modified diallylamine as an aqueous solution.

35% by mass hydrochloric acid (1 equivalent with respect to amine) was added to 78% by mass glycidol-modified diallylamine. Thereafter, water was added thereto such that the concentration became 50% by mass. The resulting solution was heated to 60° C., 2,2'-azobis(2-methyl propionamidine) dihydrochloride (6 mol % with respect to monomer) was added thereto dividedly, and polymerization was performed for 24 hours. The resulting solution was purified by electrodialysis to obtain glycidol-modified polydiallylamine as an aqueous solution.

Water was added to 43% by mass glycidol-modified polydiallylamine prepared according to the above method such that the concentration became 30% by mass, and the resulting solution was stirred at 20° C. The reaction solution had a pH of 11. Subsequently, each of 65% by mass diallyl dimethyl ammonium chloride (3 equivalents with respect to amine) and 36.04 g of 28.5% by mass APS aqueous solution (10 mol % with respect to monomer) was added thereto dividedly, and polymerization was performed for 24 hours. Thereafter, 36.04 g of 28.5% by mass APS aqueous solution (10 mol % with respect to monomer) was further added thereto dividedly, and polymerization was performed at 50° C. for 24 hours to obtain a graft polymer of glycidol-modified polydiallylamine and diallyl dimethyl ammonium chloride as an aqueous solution (weight average molecular weight: 84000).

(12) Graft Polymer of Propylene Oxide-Modified Polyethylene Imine and Diallyl Dimethyl Ammonium Chloride Propylene oxide (0.1 equivalents with respect to amine) was dropwise added to 47% by mass polyethylene imine (weight average molecular weight: 2000) while the polyethylene imine was stirred. The resulting solution was allowed to react at 20° C. for 24 hours to obtain a propylene oxide-modified polyethylene imine aqueous solution.

Water was added to 50% by mass propylene oxide-modified polyethylene imine prepared according to the above method such that the concentration became 14% by mass, and the resulting solution was stirred at 20° C. The reaction solution had a pH of 12. Subsequently, each of 65% by mass diallyl dimethyl ammonium chloride (3 equivalents with respect to amine) and 31.23 g of 28.5% by mass APS aqueous solution (10 mol % with respect to monomer) was added thereto dividedly, and polymerization was performed for 24 hours to obtain a graft polymer of propylene oxide-modified polyethylene imine and diallyl dimethyl ammonium chloride as an aqueous solution.

(13) Graft Polymer of Propylene Oxide-Modified Polyvinylamine and Diallyl Dimethyl Ammonium Chloride Propylene oxide (0.1 equivalents with respect to amine) was dropwise added to 15% by mass polyvinylamine (weight average molecular weight: 150000) while the polyvinylamine was stirred. After a reaction at 20° C. for 24 hours, the solution was concentrated to obtain a 23% by mass propylene oxide-modified polyvinylamine aqueous solution.

Water was added to 23% by mass propylene oxide-modified polyvinylamine prepared according to the above method such that the concentration became 15% by mass, and the resulting solution was stirred at 20° C. The reaction solution had a pH of 12. Subsequently, each of 65% by mass diallyl dimethyl ammonium chloride (3 equivalents with respect to amine) and 31.23 g of 28.5% by mass APS aqueous solution (10 mol % with respect to monomer) was added thereto dividedly, and polymerization was performed for 24 hours to obtain a graft polymer of propylene oxide-modified polyvinylamine and diallyl dimethyl ammonium chloride as an aqueous solution.

(14) Graft Polymer of Propylene Oxide-Modified Polydiallylamine and Diallyl Dimethyl Ammonium Chloride Water was added to diallylamine such that the concentration became 78% by mass, and propylene oxide (0.1 equivalents with respect to amine) was dropwise added thereto while the solution was cooled with ice water and was stirred. The solution was allowed to react at 20° C. for 24 hours to obtain propylene oxide-modified diallylamine as an aqueous solution.

35% by mass hydrochloric acid (1 equivalent with respect to amine) was added to 79% by mass propylene oxide-modified diallylamine to obtain 59% by mass propylene oxide-modified diallylamine hydrochloride as an aqueous solution. Water was added to the resulting 41.33 g of 59% by mass propylene oxide-modified diallylamine hydrochloride such that the concentration became 7% by mass, and the resulting solution was heated to 60° C. Thereafter, 123.99 g of 59% by mass propylene oxide-modified diallylamine hydrochloride and 2,2'-azobis(2-methyl propionamidine) dihydrochloride (5.6 mol % with respect to monomer) were added thereto dividedly, and polymerization was performed for 24 hours. The resulting solution was purified by electrodialysis to obtain propylene oxide-modified polydiallylamine as an aqueous solution.

Water was added to 30% by mass propylene oxide-modified polydiallylamine prepared according to the above method such that the concentration became 24% by mass, and the resulting solution was stirred at 20° C. The reaction solution had a pH of 12. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly, and polymerization was performed at 60° C. for 24 hours to obtain a graft polymer of propylene oxide-modified polydiallylamine and diallyl dimethyl ammonium chloride as an aqueous solution (weight average molecular weight: 19000).

(15) Graft Polymer of Propylene Oxide-Modified Polyallylamine and Diallyl Dimethyl Ammonium Chloride performed at 60° C. for 24 hours to obtain a graft polymer of propylene oxide-modified polyallylamine and diallyl dimethyl ammonium chloride as an aqueous solution (weight average molecular weight: 16000).

(16) Graft Polymer of Propylene Oxide-Modified Polyallylamine and 2-Vinylpyridine Water was added to propylene oxide-modified polyallylamine prepared in a similar manner to (3) such that the concentration became 20% by mass. Subsequently, 2-vinylpyridine (0.3 equivalents with respect to amine) was added thereto, and the resulting solution was stirred at 20° C. The reaction solution had a pH of 12. Thereafter, 12.01 g of 28.5% by mass APS aqueous solution (20 mol % with respect to monomer) was dropwise added thereto, and polymerization was performed for 24 hours to obtain a graft polymer of propylene oxide-modified polyallylamine and 2-vinylpyridine. The graft polymer had an average particle diameter of 225 nm.

The resulting graft polymer was estimated to have the following structure from starting raw materials or the like (in the following general formula, q is an integer of from 0 to 3,000, r is an integer of from 0 to 3,000, s is an integer of from 0 to 3,000, t is an integer of from 0 to 10,000, u is an integer of from 0 to 10,000, and w is an integer of from 0 to 10,000).

[FORMULA 24]

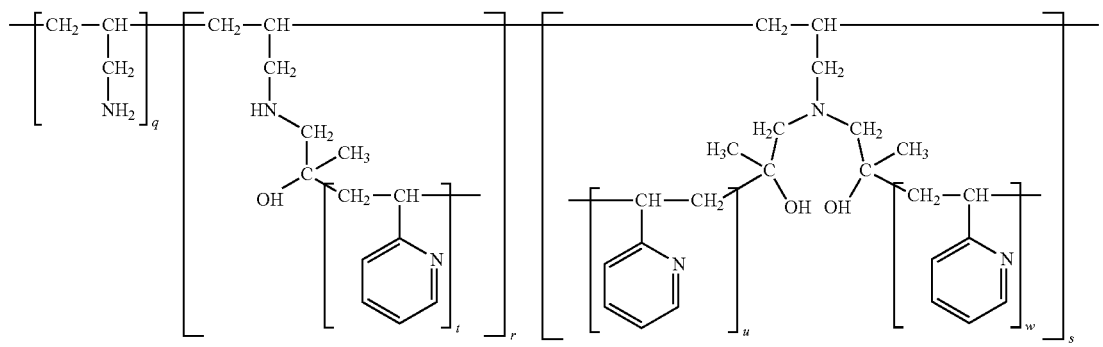

(Weight Average Molecular Weight: 2000, Use of Propylene Oxide-Modified Polyallylamine in which Propylene Oxide has been Added in an Amount of 0.1 Equivalents with Respect to Amine)

Propylene oxide (0.1 equivalents with respect to amine) was dropwise added to 15% by mass polyallylamine (weight average molecular weight: 1600) while the polyallylamine was cooled with ice water and was stirred. After a reaction at 20° C. for 24 hours, the solution was concentrated to obtain propylene oxide-modified polyallylamine as an aqueous solution.

Water was added to 30% by mass propylene oxide-modified polyallylamine prepared according to the above method such that the concentration became 18% by mass, and the resulting solution was stirred at 20° C. The reaction solution had a pH of 10. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly, and polymerization was A "sample" is a mixture which is suspected to include a "target" as a detection target. The "sample" is derived from a living body including a human (for example, blood, saliva, a bodily fluid, or a body tissue), environment (for example, soil, seawater, or environmental water (hot spring water, bath water, or cooling tower water)), or an artificial or natural product (for example, processed food such as bread, fermented food such as yogurt, a cultivated plant such as rice or wheat, a microorganism, or a virus).

The "sample" may be a product obtained by purifying and separating these as necessary. Examples thereof include blood plasma and blood serum obtained from blood.

A metal ion salt may be added to the "sample".

The "sample" may contain a surfactant, and the surfactant may be added before the "target" is detected. Examples of the surfactant include a Triton (registered trademark) surfactant (poly(oxyethylene) octylphenyl ether or the like), a Tween (registered trademark) surfactant (polyoxyethylene sorbitan fatty acid ester or the like), a Brij (registered trademark) surfactant (polyoxyethylene alkyl ether or the like), sucrose laurate (Dojindo), saponin (Sigma-Aldrich), BPSH (NIKKOL), NOIGEN TDS-70 (Dai-ichi Kogyo Seiyaku Co., Ltd.), and TritonX-705 (Sigma-Aldrich).

The "target" is an object to be detected by the present invention. The "target" is not limited, but preferably can have a minus charge. Examples thereof include a cell, fungi, bacteria, a virus, a degradation product thereof, a peptide, and a nucleic acid.

The cell may be not only a cell present in a living body but also a cultured cell. The cell may be not only a normal cell but also a cancer cell (for example, blood circulating tumor cell (CTC)).

The fungi is a generic name of an organism generally called a mushroom, mold, or yeast. Examples thereof include *Trichophyton, candida*, and *Aspergillus*.

Each of the bacteria is a procaryote having a cell membrane. Examples thereof include *Staphylococcus aureus, Escherichia coli, Salmonella, Pseudomonas aeruginosa, Vibrio cholerae, Shigella, Bacillus anthracis, Mycobacterium tuberculosis, Clostridium botulinum*, tetanus bacteria, and streptococci.

The virus is a minute structure capable of self-replicating using a cell of another organism, and is formed of a protein shell and a nucleic acid contained therein. Examples thereof include norovirus, rotavirus, influenza virus, adenovirus, coronavirus, measles virus, rubella virus, hepatitis virus, herpes virus, and HIV.

The degradation products of the cell, the fungi, the bacteria, and the virus are substances for constitution thereof, and may contain a phosphoric acid lipid of a membrane fraction or the like of organelles (nucleus, Golgi apparatus, mitochondria, or the like), the cell, the fungi, or the bacteria (including an inside out vesicle), or may be a complex of the substances constituting the cell, the fungi, the bacteria, and the virus, or the like. The degradation products of the cell, the fungi, the bacteria, and the virus may be a minute membrane vesicle (for example, Endotherial Microparticle: EMP) or a vesicle generated by apoptosis, although the minute membrane vesicle or the vesicle is not present in a normal cell.

The peptide contains a complete protein meaning a series of molecules formed by connecting various amino acids and functioning in a living body, and may include various so-called post-translational modifications (for example, glycosylation: sugar chain modification).

The nucleic acid may be a deoxyribonucleotide (DNA), a ribonucleotide (RNA), or a mixture or a bound complex thereof. A constituent base thereof is a naturally existing nucleotide, for example, guanine (G), adenine (A), thymine (T), cytosine (C), or uracil (U). However, any other natural or artificial modified base may be contained. Here, the "modified base" means a base obtained by subjecting the above five nucleotides to chemical modification. Examples thereof include methyl cytidine, pseudouridine, 4-thiouridine, dihydrouridine, queuosine, and hypoxanthine (inosine (I)), although the modified base is not limited thereto. cDNA produced by a reverse transcription reaction using RNA as a template is also included.

"Under a basic condition" means that the pH is 8 or more, preferably 9 or more, more preferably 10 or more, and still more preferably 11 or more. It is preferable to form the basic condition using a basic solution. Examples of the basic solution include a weak base, a strong base such as a NaOH aqueous solution, and a buffer with a buffer capacity at a pH of 8 or more, (for example, a glycine buffer, CHES, or CAPS).

A form in which a cationic graft polymer is "brought into contact" with a sample containing a target substance includes a form in which a cationic graft polymer is added to a sample in addition to a form in which a cationic graft polymer solution is added to a sample.

The "binding" means a state in which a cationic graft polymer interacts with a target by a coordination bond and/or an ionic bond.

"Separating" a bound complex means unwinding a bound complex under an acidic condition or unwinding the above "binding" of a cationic graft polymer and a target in the presence of a chelating agent.

"Under an acidic condition" means that the pH is 7 or less, preferably 6 or less, and more preferably 5 or less. It is preferable to form the acidic condition using an acidic solution. Examples of the acidic solution include a glycine buffer, a formic acid solution, and an acetic acid solution.

Examples of the chelating agent include ethylene diamine tetraacetic acid (EDTA) and glycol ether diamine tetraacetic acid (EGTA). The pH is not limited as long as a proton in a chelating agent is detached at the pH, but the pH is preferably from 6.0 to 8.0.

"Eluting the target substance" means that the target substance is dissolved in a proper solution after the above "separation" reaction. When the target substance is a living cell, "eluting the target substance" means collection without breaking a cell membrane.

Examples of the divalent or trivalent metal ion include $Mg^{2+}$, $Ba^{2+}$, $Ca^{2+}$, $Sr^{2+}$, $Ni^{2+}$, $Zn^{2+}$, $Mn^{2+}$, $Co^{2+}$, $Fe^{2+}$, $Fe^{3+}$, $Al^{3+}$, $Cr^{3+}$, $Cu^{2+}$, $Cd^{2+}$, and $Sn^{2+}$.

"Fixing to a solid phase surface" means that the "cationic graft polymer" is distributed unevenly. Specifically, "fixing to a solid phase surface" means that the "cationic graft polymer" is fixed to a surface of glass, a nylon membrane, a semiconductor wafer, micro beads, latex beads, magnetic beads, colloidal particles, or the like, or the surface is coated with the "cationic graft polymer", although not being limited thereto. As a method for fixing, the "cationic graft polymer" may be fixed directly to a surface of glass or the like using a known technique, or may be fixed indirectly thereto through a linker molecule. A cationic graft polymer fixed to a solid phase surface may be synthesized by polymerizing a monomer on the solid phase surface.

"Fixing to a solid phase surface" may also mean that the "cationic graft polymer" is filled in a chromatographic column or the like.

"Washing a bound complex" means an operation for removing impurities non-specifically bound to a cationic graft polymer while the binding between the "cationic graft polymer" and the "target substance" is maintained. For washing, the same solution as the solution used in the binding reaction may be used, or another solution may be used. A physiological saline solution or an alcohol may be used.

Examples of "aggregating a cationic graft polymer not bound to a target substance" include separating a cationic graft polymer by a hydrophobic interaction or aggregating a cationic graft polymer by an ionic interaction with a polyanion as a counter ion or an anionic surfactant for separating. More specifically, a cationic graft polymer is aggregated by a hydrophobic interaction of acetonitrile or an ionic interaction with a polyanion or an ionic surfactant using an aggregation solution (including an aprotic polar solvent (such as acetonitrile), an anionic surfactant (such as sodium octanesulfonate or sodium decanesulfonate), and a polyanion (carboxymethylated polyallylamine: CMPAA)).

The above "cationic graft polymer", "reaction solution", "washing solution", "dispersion solution", and "aggregation solution" may include not only a liquid type (an emulsified type in a case of the "cationic graft polymer") but also a product obtained by drying the solution.

EXAMPLES

The present invention will be described in more detail with the following Examples, Comparative Examples, and Reference Examples, but is not limited thereto.

Example 1

Separation of *Escherichia coli* and Confirmation of Recovery
1. Method
A recovery of *Escherichia coli* collected with a cationic graft polymer was determined using a blood cell analyzer (Sysmex).
Samples and reagents are as follows.
1) Sample
*Escherichia coli* was produced using a GFP expression Kit manufactured by Bio-Rad Laboratories, Inc.
The produced *Escherichia coli* was added to normal human blood serum in a necessary amount (1 to $2 \times 10^4$ cell/μL), and the resulting mixture was used as a sample.
2) Reagent
I: reaction solution: 1M glycine-NaOH pH 11.0, 3M magnesium chloride
II: dispersion solution: 500 mM glycine-HCl pH 5.0
3) Cationic Graft Polymer
Propylene oxide (0.1 equivalents with respect to amine) was dropwise added to 20% by mass polyallylamine (weight average molecular weight: 3000) while the polyallylamine was cooled with ice water and was stirred. After a reaction at 20° C. for 24 hours, the solution was concentrated to obtain propylene oxide-modified polyallylamine as an aqueous solution.
Water was added to the propylene oxide-modified polyallylamine such that the concentration became 20% by mass, then styrene (0.3 equivalents with respect to amine) was added thereto, and the resulting solution was stirred at 20° C. Thereafter, 12.01 g of an ammonium persulfate (APS) aqueous solution at a concentration of 28.5% by mass (20 mol % with respect to monomer) was added thereto, and polymerization was performed for 24 hours. Thereafter, the resulting solution was heated at 70° C. for 24 hours to obtain a cationic graft polymer of propylene oxide-modified polyallylamine and styrene (average particle diameter: 120 nm) (the above (3) graft polymer of propylene oxide-modified polyallylamine and styrene).
4) Blood Cell Analyzer
*Escherichia coli* is detected in a platelet (PLT) using the blood cell analyzer.
Measurement was performed according to a protocol of the blood cell analyzer.
Separation of *Escherichia coli* and confirmation of a recovery were performed as follows.
500 μL of a sample, 50 μL of a 20% cationic graft polymer, and 100 μL of a reaction solution were mixed and allowed to react for one minute. Thereafter, the resulting product was centrifuged for 30 seconds by a tabletop small centrifugal machine to obtain a precipitation pellet. The supernatant was collected, and the resulting precipitation pellet was completely dispersed with 500 μL of a dispersion solution to obtain a suspension. A recovery of *Escherichia coli* for the supernatant or the suspension was determined using the blood cell analyzer. As a control, *Escherichia coli* before a reaction with a cationic graft polymer was used.

2. Result
Table 1 shows results of measurement using the blood cell analyzer.

TABLE 1

|  | Example 1 $10^4$ cell/μL | Control $10^4$ cell/μL |
|---|---|---|
| supernatant | 0.2 | 1.7 |
| suspension | 1.2 | — |

The results in Table 1 indicate that the recovery was about 70%, which was an excellent recovery.

Example 2

Confirmation of Survival (Viability) of Separated *Escherichia coli*
1. Method
*Escherichia coli* in blood was separated with a cationic graft polymer, and confirmation of survival of the separated *Escherichia coli* was performed by culture.
Samples and reagents are as follows.
1) Sample
*Escherichia coli* produced using the GFP expression Kit manufactured by Bio-Rad Laboratories, Inc. was added to normal human blood serum in a necessary amount in a similar manner to Example 1, and the resulting mixture was used as a sample.
2) Reagent
I: reaction solution: 1M glycine-NaOH pH 11.0, 3M magnesium chloride
II: dispersion solution: 500 mM glycine-HCl pH 5.0
3) Cationic Graft Polymer
A cationic graft polymer was prepared in a similar manner to Example 1.
Separation of *Escherichia coli* and confirmation of survival (viability) thereof were performed as follows.
500 μL of a sample, 50 μL of a 20% cationic graft polymer, and 100 μL of a reaction solution were mixed and allowed to react for one minute. Thereafter, the resulting product was centrifuged for 30 seconds by a tabletop small centrifugal machine to obtain a precipitation pellet. The supernatant was removed, and the resulting precipitation pellet was completely dispersed with 500 μL of a dispersion solution to obtain a suspension (FIG. 2). Five thousandth of each of the supernatant and the suspension was cultured at 37° C. for 18 hours using a LB bacteria culture agar medium, and confirmation of survival was performed (FIG. 3).
As Comparative Examples, a precipitation pellet was obtained in a similar manner to Examples. Thereafter, each of 500 μL of a 1.5 M NaCl solution (Comparative Example 1) and 500 μL of a 1.5% TritonX-100 (Comparative Example 2) was added thereto, and the pellet was completely dispersed. Each of the supernatants and the dispersion solutions was cultured in a similar manner to Examples, and viability was confirmed.

2. Result

Table 2 shows culture results.

TABLE 2

|  | Example 2 colony | Comparative Example 1 colony | Comparative Example 2 colony |
| --- | --- | --- | --- |
| supernatant | 0 | 0 | 0 |
| suspension | 112 | 53 | 16 |

The results in Table 2 indicate that bacteria can be collected while being alive without subjecting the bacteria to bacteriolysis by using the method of the present invention.

Example 3

Measurement Using Mass Spectrometry

1. Method

*Escherichia coli* collected with a cationic graft polymer was subjected to bacterial identification using a MALDI TOF (matrix assisted laser desorption ionization time-of-flight) mass spectrometry, MALDI BioTyper (registered trademark) (Bruker Daltonics K.K.).

Samples and reagents are as follows.

1) Sample

*Escherichia coli* was produced using a GFP expression Kit manufactured by Bio-Rad Laboratories, Inc.

The produced *Escherichia coli* was added to a physiological saline solution in a necessary amount, and the resulting mixture was used as a sample.

2) Reagent

I: reaction solution: 1M glycine-NaOH pH 11.0, 3M magnesium chloride

II: dispersion solution: 70% formic acid

III: aggregation solution: 100% acetonitrile

3) Cationic Graft Polymer

A cationic graft polymer was prepared in a similar manner to Example 1.

4) Mass Spectrometry

Matrix HCCA portioned manufactured by Bruker Daltonics K.K. was used as a matrix.

Measurement was performed according to a protocol of MALDI Bio Typer (registered trademark). Determination of bacterial identification was evaluated by a score specified by BioTyper (registered trademark).

Separation of *Escherichia coli* and measurement using the mass spectrometry were performed as follows.

Figure 1:
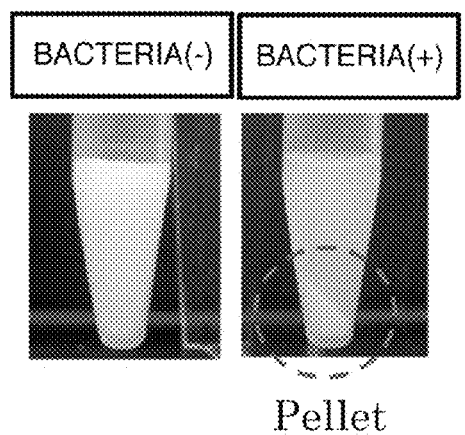
FIG. 1 Precipitation pellet of bound complex of *Escherichia coli* and cationic graft polymer

500 µL of a sample, 50 µL of a 20% cationic graft polymer, and 100 µL of a reaction solution were mixed and allowed to react for one minute. Thereafter, the resulting product was centrifuged for 30 seconds by a tabletop small centrifugal machine to obtain a precipitation pellet (FIG. 1). The supernatant was removed, the resulting precipitation pellet was completely dispersed with 50 µL of a dispersion-extraction solution, and a protein in a bacterial cell was extracted. Thereafter, 200 µL of an aggregation solution was added thereto, and the resulting mixture was centrifuged for 30 seconds by a tabletop small centrifugal machine to precipitate a cationic graft polymer. The supernatant was collected to be used as a sample for measurement using the mass spectrometry.

2. Result

Table 3 shows a result of measurement using the mass spectrometry.

TABLE 3

| Example 3 score |
| --- |
| 2.12 |

The result in Table 3 indicates that the identification score was 1.7 or more, which was an excellent identification accuracy. This result indicates that it is possible to extract a protein in *Escherichia coli* and to perform measurement using the mass spectrometry.

Examples 4 and 5

Separation of Nucleic Acid in Blood Serum and Confirmation of Recovery

1. Method

A nucleic acid added to blood serum was separated with a cationic graft polymer. The resulting nucleic acid was subjected to agarose electrophoresis, stained with SYBR Safe (invitrogen), and was detected by LAS4000 (GE). The recovery was determined from a fluorescence intensity of a spot.

Samples and reagents are as follows.

1) Sample

As a nucleic acid, a plasmid and a genome were used. The plasmid was extracted from *Escherichia coli* (Example 4), and the genome was extracted from a Hela cell (Example 5). The extracted plasmid solution was cultured using a LB bacteria culture agar medium, and a colony was not formed. No contamination of *Escherichia coli* was thereby confirmed. No contamination of the cell in the extracted genome solution was confirmed using a fluorescence microscope.

The extracted DNA was added to normal human blood serum in a necessary amount to be used as a sample. As a control, normal human blood serum containing no DNA was used.

2) Reagent

I: reaction solution: 1M glycine-NaOH pH 11.0, 3M magnesium chloride

II: dispersion solution: 500 mM EDTA-2Na pH 8.0

3) Cationic Graft Polymer

A cationic graft polymer was prepared in a similar manner to Example 1.

4) Electrophoresis

A 1.0% agarose gel was used.

For adjusting a sample for electrophoresis, 6× Loading Dye (TOYOBO) was used.

Separation of a nucleic acid and a detection method thereof were performed as follows.

500 µL of a sample, 50 µL of a 20% cationic graft polymer, and 100 µL of a reaction solution were mixed and allowed to react for one minute. Thereafter, the resulting product was centrifuged for 30 seconds by a tabletop small centrifugal machine to obtain a precipitation pellet. To the supernatant and the suspension, 500 µL of a nucleic acid extraction reagent phenol-chloroform-isoamyl alcohol (25:24:1) manufactured by Nacalai Tesque, Inc. was added, and was separated into a phenol phase and an aqueous phase. 300 µL of DNA in the aqueous phase was collected, 600 µL of ethanol and 30 µL of a sodium acetate aqueous solution were mixed, and DNA was precipitated by ethanol precipitation. The precipitate was suspended in 100 μL of distilled water, and was mixed with Loading Dye to be used as a sample for electrophoresis. Electrophoresis was performed using a 1% agarose gel. Staining was performed with SYBR Safe, and then was detected fluorescently by LAS4000 (FIG. 4).

2. Result

Table 4 shows results of a DNA collected amount.

TABLE 4

|  | Example 4 μg/mL | Example 5 μg/mL |
|---|---|---|
| before treatment | 54 | 280 |
| after treatment | 32 | 112 |
| recovery | 60% | 40% |

The results in Table 4 indicate that the recovery of the plasmid DNA was 60% and the recovery of the genome DNA was 40%.

Example 6

Separation of Cell in Blood Serum, Recovery, and Confirmation of Three-Dimensional Structure and Surface Structure 1. Method A cell added to blood serum was separated with a cationic graft polymer. The recovery of the cell was confirmed using the blood cell analyzer (Sysmex). An antigen-antibody reaction on a surface of the cell was confirmed using a fluorescence microscope (Life technologies).

Samples and reagents are as follows.

1) Sample

As the cell, a Hela cell was used, and the Hela cell was added to normal human blood serum in a necessary amount (1 to $2 \times 10^6$ cell/mL), and the resulting mixture was used as a sample.

2) Reagent

I: reaction solution: 1M glycine-NaOH pH 11.0, 3M magnesium chloride

II: dispersion solution: 500 mM EDTA-2Na pH 8.0

3) Cationic Graft Polymer

A cationic graft polymer was prepared in a similar manner to Example 1.

4) Blood Cell Analyzer

The cell was measured as WBC.

Measurement was performed according to a protocol of the blood cell analyzer in a similar manner to Example 1.

5) Antibody

As a primary antibody, each of an anti-human CD 146 (MCAM) and a monoclonal antibody (N 1238) (MONO-SAM) was diluted by 50 times to be used.

As a secondary antibody, Anti-Mouse IgG Alexa Fluor 594 (Life Technologies) was diluted by 500 times to be used.

The primary antibody and the secondary antibody were allowed to react by inversion mixing for one hour in a light-shielding state to prepare a fluorescent labeled antibody.

Methods for separating and detecting a cell were performed as follows.

500 μL of a sample, 50 μL of a 20% cationic graft polymer, and 100 μL of a reaction solution were mixed and allowed to react for one minute. Thereafter, the resulting product was centrifuged for 30 seconds by a tabletop small centrifugal machine to obtain a precipitation pellet. The supernatant was collected, and the resulting precipitation pellet was completely dispersed with 500 μL of a dispersion solution (FIG. 5). A recovery for the collected supernatant or the resulting suspension was measured using the blood cell analyzer. As a control, a cell before a reaction with a cationic graft polymer was used.

Subsequently, the suspension was mixed with a fluorescent labeled antibody, and was allowed to react by inversion mixing for one hour in a light-shielding state to confirm an antigen-antibody reaction using a fluorescence microscope (FIG. 6).

2. Result

Table 5 shows WBC measured values using the blood cell analyzer.

TABLE 5

|  | Example 6 $10^2$ cell/ μL | Control $10^2$ cell/ μL |
|---|---|---|
| supernatant | 0.1 | 17.5 |
| suspension | 17.1 | — |

The results in Table 5 indicate that the recovery was about 98%, which was an excellent recovery.

The blood cell analyzer measures a substance having a nucleus as WBC. Therefore, a cell can be collected while maintaining a three-dimensional structure by using the method of the present invention.

An antigen-antibody reaction between the Hela cell and the MCAM antibody was confirmed using a fluorescence microscope. These results indicate that the cell can be collected while maintaining a surface structure thereof.

Example 7

Separation of Vesicle in Blood Serum, Recovery, and Confirmation of Three-Dimensional Structure and Surface Structure 1. Method A vesicle added to blood serum was separated with a cationic graft polymer. The recovery of the vesicle was confirmed using the blood cell analyzer. Whether the separated vesicle maintained the three-dimensional structure and the surface structure was confirmed using a fluorescence microscope (Life technologies).

Samples and reagents are as follows.

1) Sample

A vesicle was produced by crushing a Hela cell using a sonicator.

In order to observe the vesicle using a fluorescence microscope, the cell was crushed in a fluorescent dye (DyLight, Ex/Em: 493/518) aqueous solution included in a DyLight 488 Antibody Labeling kit (Thermo), and the fluorescent dye was incorporated in the vesicle.

The produced vesicle was added to normal human blood serum in a necessary amount to be used as a sample.

2) Reagent

I: reaction solution: 1M glycine-NaOH pH 11.0, 3M magnesium chloride

II: dispersion solution: 500 mM EDTA-2Na pH 8.0

3) Cationic Graft Polymer

A cationic graft polymer was prepared in a similar manner to Example 1.

4) Blood Cell Analyzer

The vesicle was measured as WBC.

Measurement was performed according to a protocol of the blood cell analyzer in a similar manner to example 1.

5) Antibody

As a primary antibody, each of an anti-human CD 146 (MCAM) and a monoclonal antibody (N 1238) (MONOSAM) was diluted by 50 times to be used.

As a secondary antibody, Anti-Mouse IgG Alexa Fluor 594 (Life Technologies) was diluted by 500 times to be used.

The primary antibody and the secondary antibody were allowed to react by inversion mixing for one hour in a light-shielding state to prepare a fluorescent labeled antibody.

Methods for separating and detecting a vesicle were performed as follows.

500 μL of a sample, 100 μL of a 10% cationic graft polymer, and 50 μL of a reaction solution were mixed and allowed to react for one minute. Thereafter, the resulting product was centrifuged for 30 seconds by a tabletop small centrifugal machine to obtain a precipitation pellet. The supernatant was collected, and the resulting precipitation pellet was completely dispersed with 500 μL of a dispersion solution to obtain a suspension (FIG. 7). A recovery for the collected supernatant or the resulting suspension was measured using the blood cell analyzer. As a control, a vesicle before a reaction with a cationic graft polymer was used.

Subsequently, the suspension was mixed with a fluorescent labeled antibody, and was allowed to react by inversion mixing for one hour in a light-shielding state to confirm an antigen-antibody reaction using a fluorescence microscope (FIG. 8).

2. Result

Table 6 shows vesicle measured values using the blood cell analyzer.

TABLE 6

|  | Example 7 $10^2$ cell/ μL | Control $10^2$ cell/ μL |
| --- | --- | --- |
| supernatant | 0.1 | 22.5 |
| suspension | 18.5 | — |

The results in Table 6 indicate that the recovery of the vesicle was 82%, which was an excellent recovery.

A state in which a fluorescent dye was incorporated in the vesicle in the suspension and an edge of the vesicle was surrounded by a fluorescent labeled antibody was confirmed using a fluorescence microscope. These results indicate that the vesicle can be collected while maintaining a three-dimensional structure and a surface structure thereof.

Reference Example 1

Separation of Virus Particle and Collecting Confirmation

1. Method

As a model of a virus formed of a protein shell and a nucleic acid contained therein, a bacteriophage was used. A phage solution having a constant titer was adjusted, a bacteriophage was collected by the method of the present invention, and the titer after collection was calculated by counting a plaque in which *Escherichia coli* was subjected to bacteriolysis.

1) Sample
   bacteriophage
   host *Escherichia coli*
2) Reagent
   I: reaction solution: 1M glycine-NaOH pH 11.0, 3M magnesium chloride
   II: dispersion solution: 500 mM glycine-HCl pH 5.0

3) Cationic Graft Polymer

A cationic graft polymer was prepared in a similar manner to Example 1.

Methods for separating and detecting the bacteriophage were performed as follows.

500 μL of a bacteriophage sample, 100 μL of a 10% cationic graft polymer, and 50 μL of a reaction solution were mixed and allowed to react for one minute. Thereafter, the resulting product was centrifuged for 30 seconds by a tabletop small centrifugal machine to obtain a precipitation pellet. The supernatant was collected, and the resulting precipitation pellet was completely dispersed with 500 μL of a dispersion solution to obtain a suspension. The resulting solution was serially diluted. The diluted solution was mixed with a host *Escherichia coli* culture solution. The resulting mixture was added to soft agar, and was cultured on an agar plate overnight. The titer of a collected phage is calculated from the number of the plaque.

Example 8

Confirmation of Survival (Viability) of Bacteria Collected Using Surfactant-Containing Solution 1. Method

*Escherichia coli* precipitated on a separating agent in a blood collection tube is collected while being alive using a non-ionic surfactant-containing solution.

Samples and reagents are as follows.

1) Sample

*Escherichia coli* was produced using a GFP expression Kit manufactured by Bio-Rad Laboratories, Inc.

The produced *Escherichia coli* was added to a physiological saline solution in an amount of $2 \times 10^8$ cell/mL, and the resulting mixture was used as a sample.

2) Reagent

I: 1% surfactant solution

In Experiments 1 to 6, sucrose laurate (Dojindo), saponin (Sigma-Aldrich), BPSH (NIKKOL), NOIGEN TDS-70 (Dai-ichi Kogyo Seiyaku Co., Ltd.), Triton X-705 (Sigma-Aldrich), and CHAPS (Dojindo) were used as surfactants.

TABLE 7

| classification | surfactant | |
| --- | --- | --- |
| nonionic | Experiment 1 | sucrose laurate |
|  | Experiment 2 | saponin |
|  | Experiment 3 | BPSH |
|  | Experiment 4 | NOIGEN TDS-70 |
|  | Experiment 5 | Triton X-705 |
| zwitterionic | Experiment 6 | CHAPS |

II: reaction solution: 1M glycine pH 11.0, 3M magnesium chloride

III: dispersion solution: 500 mM glycine pH 5.0

3) Cationic Graft Polymer

A cationic graft polymer was prepared in a similar manner to Example 1.

Collection of a bacterial cell and confirmation of survival (viability) thereof were performed as follows.

To a blood collection tube, 3 mL of a bacterial solution in which *Escherichia coli* was dispersed in a physiological saline solution was added, and was centrifuged at 3000 rpm for five minutes. Thereafter, the supernatant was removed. Subsequently, 0.5 mL of a 1% surfactant solution was added to the blood collection tube, and a bacterial cell precipitated on a surface of a separating agent was dispersed.

The bacterial cell suspension was allowed to stand at 20° C. for 30 minutes and three hours. Thereafter, 100 μL of a 10% cationic graft polymer and 100 μL of a reaction solution were mixed and allowed to react for one minute. Thereafter, the resulting product was centrifuged for 30 seconds by a tabletop small centrifugal machine to obtain a precipitation pellet. The supernatant was removed, and the resulting precipitation pellet was completely dispersed with 500 μL of a dispersion solution to obtain a suspension. One hundredth of the suspension was cultured at 37° C. for 18 hours using a LB bacteria culture agar medium, and the number of living bacteria was confirmed by the number of colonies.

As a control, a physiological saline solution was used in place of the surfactant solution (Control 1).

2. Result

Table 8 shows the number of colonies in a sample after culture.

TABLE 8

| | | the number of colonies | |
|---|---|---|---|
| | | allowed to stand for 30 minutes | allowed to stand for 3 hours |
| Control 1 | physiological saline solution | >5000 | >5000 |
| Experiment 1 | sucrose laurate | 4000 | 3200 |
| Experiment 2 | saponin | 2200 | 1864 |
| Experiment 3 | BPSH | 712 | 540 |
| Experiment 4 | NOIGEN XL60 | 196 | 112 |
| Experiment 5 | TritonX-705 | 2016 | 1224 |
| Experiment 6 | CHAPS | 84 | 61 |

When the non-ionic surfactants used in Experiments 1 to 5 were used, particularly when sucrose laurate was used, bacteria can be collected while being alive.

Example 9

Measurement of *Escherichia coli* Collected Using Surfactant-Containing Solution Using Mass Spectrometry 1. Method

*Escherichia coli* precipitated on a separating agent in a blood collection tube was collected using a surfactant-containing solution, and was allowed to react with a cationic polymer. Thereafter, the reaction product was washed with 70% acetonitrile. A sample capable of suppressing an effect of a blood component and being measured using the mass spectrometry was thereby prepared.

Samples and reagents are as follows.

1) Sample

*Escherichia coli* was produced using a GFP expression Kit manufactured by Bio-Rad Laboratories, Inc.

Whole blood and produced *Escherichia coli* were added to a culture bottle for bacterial culture (BD) in an amount of $2 \times 10^8$ cell/mL to be used as a sample.

2) Reagent

I: collection solution: 0.1% surfactant

II: reaction solution 1: 1 M glycine pH 11.0

III: reaction solution 2: 3 M magnesium chloride

IV: washing solution: 70% acetonitrile

V: extraction solution: 70% formic acid

VI: separation solution: 100% acetonitrile

3) Cationic Graft Polymer

A cationic graft polymer was prepared in a similar manner to Example 1.

4) Electrophoresis

E-R155e-PAGEL 15% gel (ATTO) was used.

2D-silver staining reagent II (Cosmo Bio) was used for gel staining.

5) Mass Spectrometry

Measurement was performed in accordance with an instruction manual using an Auto FlexII flex Control 2.0 (Bruker).

Flex Analysis was used for mass spectral analysis.

Removal of a blood component was confirmed as follows.

Blood was collected. To a culture bottle, 10 mL of the collected blood was added, and 3 mL was transferred to a blood collection tube therefrom. The blood collection tube was centrifuged at 3000 rpm for five minutes to separate a blood cell component from a bacterial cell. To the blood collection tube, 500 μL of a collection solution was added, and *Escherichia coli* adsorbed by a surface of a separating agent in the blood collection tube was collected in a 1.5 mL tube. Here, in Experiments 7 to 12, sucrose laurate, NOIGEN XL60, saponin, BPSH, TritonX-705, and CHAPS were used as surfactants contained in the collection solution.

As Control 2, distilled water was used in place of the surfactant added to the collection solution for examination. In the tube containing the collection solution, 100 μL of a 10% cationic graft polymer, 100 μL of reaction solution 1, and 100 μL of reaction solution 2 were mixed, and were allowed to react for one minute. Thereafter, the resulting product was centrifuged for 30 seconds by a tabletop small centrifugal machine to obtain a precipitation pellet. The supernatant was removed. The resulting precipitation pellet was completely dispersed with 500 μL of a washing solution, and was centrifuged for 30 seconds by a tabletop small centrifugal machine to obtain a precipitation pellet. The supernatant was collected in a 1.5 mL tube to be used as sample 1. The precipitation pellet was completely dispersed with 50 μL of an extraction solution. Thereafter, 150 μL of an aggregation precipitation solution was added thereto, and the resulting mixture was centrifuged for 30 seconds by a tabletop small centrifugal machine. The supernatant was transferred to a new 1.5 mL tube to be used as sample 2.

Mass spectrum thereof was measured using an Auto FlexII.

In order to check an effect of contaminants, confirmation by electrophoresis was performed. As a sample used for measurement, Control 2 and samples 1 and 2 obtained in Experiments 7 to 12 were centrifuged at 15000 rpm for 30 minutes. The supernatants were collected, and were lyophilized overnight for concentration. The dried samples were dissolved in 50 μL of SDS sample Buffer to be used as a sample for electrophoresis. Electrophoresis was performed using E-R155e-PAGEL 15% gel.

2. Result

Table 9 shows results of electrophoresis.

In sample 1, major bands were confirmed around molecular weights of 10000 and 30000. This result indicates that a blood component adsorbed by a cationic polymer can be removed with a washing solution. Sample 2 had a larger number of bands of 30000 or less than Control 2. This result indicates that a protein band derived from a bacterial cell was detected by removal of the blood component with the washing solution.

Table 10 shows mass spectrum obtained using an Auto FlexII.

In order to determine whether ionization in the mass spectrometry is inhibited by a surfactant used, the mass peak number was counted with a Find Mass List function of a software for data processing flex Analysis from the obtained mass spectrum. Table 9 shows results thereof. Table 10 shows count conditions.

In order to confirm an influence avoidance effect of a blood component, a ratio of a peak intensity of a mass peak derived from the blood component with respect to a mass peak derived from a bacterial cell was determined. As the mass peak derived from the bacterial cell, 6250 m/z and 9740 m/z were selected from mass peaks detected when a colony was used as a sample. As the mass peak derived from the blood component, 15130 m/z which was a mass peak of hemoglobin was selected. Table 11 shows results thereof.

TABLE 9

|  |  | the counted number |
|---|---|---|
| Control 2 | physiological saline solution | 58 |
| Experiment 7 | sucrose laurate | 65 |
| Experiment 8 | NOIGEN XL60 | 64 |
| Experiment 9 | saponin | 31 |
| Experiment 10 | BPSH | 46 |
| Experiment 11 | TritonX-705 | 21 |
| Experiment 12 | CHAPS | 53 |

TABLE 10

| Peak Detection Algorithm | Snap |
|---|---|
| Signal Noise Threshold | 3 |
| Relative Intensity Threshold | 0 |
| Minimum Intensity Threshold | 0 |
| Maxmal Number of peaks | 100 |
| Peak width | 5 m/z |

TABLE 11

|  |  | 9738/15130 (m/z) | 6250/15130 (m/z) |
|---|---|---|---|
| Control 2 | physiological saline solution | 0.75 | 1.79 |
| Experiment 7 | sucrose laurate | 1.28 | 4.88 |
| Experiment 8 | NOIGEN XL60 | 1.44 | 1.53 |
| Experiment 9 | saponin | 0.05 | 0.81 |
| Experiment 10 | BPSH | 0.42 | 0.59 |
| Experiment 11 | TritonX-705 | 0.29 | 0.17 |
| Experiment 12 | CHAPS | 0.72 | 1.19 |

Table 9 indicates that, in Experiments 7 and 8, the counted mass peak number is larger than that in Control 2 and therefore ionization may be promoted. On the other hand, Table 9 indicates that, in Experiments 9 to 11, the counted mass peak number is smaller than that in Control 2 and therefore ionization may be inhibited.

Table 11 indicates that, in Experiments 7 and 8, a ratio between a mass peak derived from a bacterial cell and a mass peak derived from blood is 1.0 or more, and the peak derived from a bacterial cell was detected at a higher intensity than the peak derived from blood. On the other hand, Table 11 indicates that, in Experiments 9 to 12, a ratio between a mass peak derived from a bacterial cell and a mass peak derived from blood is 1.0 or less, the peak derived from blood was detected at a higher intensity than the peak derived from a bacterial cell, and the influence avoidance effect of a blood component was low.

From these results, the methods in Experiments 7 and 8 can suppress an effect of a blood component and makes measurement using the mass spectrometry possible.

Example 10A

Separation of Virus Particle and Collecting Confirmation (Additional Test of Reference Example 1)

1. Method

1) Sample

Using *Escherichia coli* phage T7 (code: 20007) purchased from NBRC (National Institute of Technology and Evaluation Center for Biotechnology), a bacteriophage was prepared in accordance with an NBRC specified protocol and a general experimental procedure, for example, "invincible biotechnical series-genetic engineering laboratory notebook (first volume)

2. Section of Bacteriophage (Yodosha)".

A dried bacterial cell was suspended in 200 µL of condensed water solution (10% polypepton, 2% Yeast extract, 1% MgSO4), and then was overlaid on a 0.6% agar medium including about $10^5$ cells of *Escherichia coli* (10% polypepton, 5% Yeast extract, 2.5% NaCl, 1% agar). This medium plate was cultured at 37° C. overnight. Agar in a portion in which a colony had not been formed was scraped off (about several cm$^2$), and was transferred to a 1.5 mL tube. Thereinto, 1 mL of 10 mM Tris-HCl (pH 7.5) was put, and the tube was shaken at 20° C. for 90 minutes. Thereafter, the resulting solution was centrifuged at 3000 rpm for 15 minutes, and the supernatant was collected to be used as a bacteriophage sample (refrigerated).

2) Reagent

I: reaction solution 1: 1 M glycine-NaOH pH 11.0

II: reaction solution 2: 3 M magnesium chloride solution

III: dispersion solution: 1 M glycine-HCl pH 5.0

3) Cationic Graft Polymer

A cationic graft polymer was prepared in a similar manner to Example 1.

Separation of a bacteriophage and titer confirmation thereof were performed as follows.

500 µL of a sample, 100 µL of a 20% cationic graft polymer, 100 µL of reaction solution 1, and 100 µL of reaction solution 2 were mixed. Thereafter, the resulting mixture was centrifuged for 30 seconds by a tabletop small centrifugal machine to obtain a precipitation pellet. The supernatant was removed, and the resulting precipitation pellet was completely dispersed with 100 µL of a dispersion solution to obtain a suspension. The suspension was mixed with an agar medium containing about $10^5$ cells of *Escherichia coli*, and was cultured at 37° C. for 18 hours to confirm bacteriolysis of *Escherichia coli* (FIG. 11).

A bacteriophage sample before reacting with a cationic graft polymer was infected with *Escherichia coli* as a positive control.

2. Result

It has been found that the bacteriophage can be separated with the graft polymer.

Example 10B

Confirmation of Survival (Viability) of Separated *Escherichia coli*

1. Method

1) Sample

*Escherichia coli* produced using the GFP expression Kit manufactured by Bio-Rad Laboratories, Inc. was added to normal human blood serum in a necessary amount in a similar manner to Example 1, and the resulting mixture was used as a sample. *Escherichia coli*: about $10^8$ cells 2) Reagent
  I: reaction solution 1: 1 M glycine-NaOH pH 11.0
  II: reaction solution 2: 3 M magnesium chloride solution
  III: dispersion solution: 1 M glycine-HCl pH 5.0
3) Cationic Graft Polymer The above (5) graft polymer of epoxy octane-modified polyallylamine and diallyl dimethyl ammonium chloride (PAAEpo-g-DADMAC) and the above (8) graft polymer of glycidyl butyrate-modified polyallylamine and diallyl dimethyl ammonium chloride (PAAGB-g-DADMAC) were used.

Specifically, water was added to 20% by mass polyallylamine such that the concentration became 13% by mass, and epoxy octane (0.1 equivalents with respect to amine) was dropwise added thereto while the solution was cooled with ice water and was stirred. After dropwise addition, the solution was allowed to react at 40° C. for 24 hours, and then was concentrated to obtain epoxy octane-modified polyallylamine as an aqueous solution. Water was added to 30% by mass epoxy octane-modified polyallylamine prepared such that the concentration became 19% by mass, and the resulting solution was stirred at 20° C. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly to obtain a graft polymer of epoxy octane-modified polyallylamine and diallyl dimethyl ammonium chloride as an aqueous solution.

Alternatively, water was added to 20% by mass polyallylamine such that the concentration became 13% by mass, and glycidyl butyrate (0.1 equivalents with respect to amine) was dropwise added thereto while the solution was cooled with ice water and was stirred. After dropwise addition, the solution was allowed to react at 40° C. for 24 hours, and then was concentrated to obtain glycidyl butyrate-modified polyallylamine as an aqueous solution. Water was added to 30% by mass glycidyl butyrate-modified polyallylamine prepared such that the concentration became 19% by mass, and the resulting solution was stirred at 20° C. Subsequently, each of 65% by mass diallyl dimethyl ammonium chloride (3 equivalents with respect to amine) and 14.42 g of 28.5% by mass APS aqueous solution (10 mol % with respect to monomer) was added thereto dividedly, and polymerization was performed for 24 hours. Thereafter, 14.42 g of 28.5% by mass APS aqueous solution (10 mol % with respect to monomer) was further added thereto dividedly to obtain a graft polymer of glycidyl butyrate-modified polyallylamine and diallyl dimethyl ammonium chloride as an aqueous solution.

The above graft polymer and latex beads produced by a known method were mixed such that the graft polymer had a final concentration of 8% and the latex beads, for example, polystyrene latex LE (average particle diameter: 120 nm, manufactured by Nittobo Medical Co., Ltd.) had a final concentration of 5% to obtain a graft polymer solution.

In addition, the above graft polymer of propylene oxide-modified polyallylamine and styrene (PAA-g-PSt) used in Example 1 was used as a positive control.

Separation of *Escherichia coli* and confirmation of survival (viability) thereof were performed as follows.

500 µL of a sample, 100 µL of the above graft polymer, 100 µL of reaction solution 1, and 200 µL of reaction solution 2 were mixed. Thereafter, the resulting product was centrifuged for 30 seconds by a tabletop small centrifugal machine to obtain a precipitation pellet. The supernatant was transferred to another centrifugation tube, and was further centrifuged at 15000 rpm for five minutes. The resulting precipitate was dispersed in 500 µL of a dispersion solution.

The precipitation pellet obtained by removing the supernatant was completely dispersed with 500 µL of a dispersion solution to obtain a suspension.

Each of 100 µL of the suspension derived from the supernatant and 100 µL of the suspension derived from the precipitation pellet was added to 5 mL of a LB solution medium, and was cultured at 37° C. for 18 hours. For confirmation of survival of *Escherichia coli*, an absorbance of each of the culture solution samples before and after the culture was measured using a spectrophotometer, and a change amount thereof was used as the amount of *Escherichia coli*.

Each of 50 µL of the suspension derived from the supernatant and 50 µL of the suspension derived from the precipitation pellet was applied onto a LB bacteria culture agar medium, and was cultured at 37° C. for 18 hours. Viability of *Escherichia coli* was confirmed by formation of a colony (FIG. 12).

As a negative control, a case containing polystyrene latex LE but not containing the above graft polymer was examined 2. Result As shown in the following Table 12, it has been found that a graft polymer not forming a particle can separate and concentrate a target substance.

TABLE 12

| kind of polymer | pellet | | | sup | | | pellet/ | |
| | before culture | after culture | Δ | before culture | after culture | Δ | sup Δ | recovery (%) |
| --- | --- | --- | --- | --- | --- | --- | --- | --- |
| PAAGB-g-DADMAC + latex | 0.48 | 1.12 | 0.64 | 0.29 | 0.32 | 0.03 | 19.5 | 34.8 |
| PAAEpo-g-DADMAC + latex | 0.47 | 1.60 | 1.13 | 0.10 | 0.09 | −0.01 | 94.1 | 61.2 |
| only latex (negative control) | 0.04 | 0.07 | 0.03 | 0.04 | 0.09 | 0.05 | 0.7 | 1.8 |
| PAA-g-PSt (positive control) | 0.36 | 1.45 | 1.09 | 0.09 | 0.14 | 0.05 | 21.8 | 59.0 |

Example 11

Confirmation of Survival (Viability) of Separated *Escherichia coli*

1. Method
1) Sample

*Escherichia coli* produced using the GFP expression Kit manufactured by Bio-Rad Laboratories, Inc. was added to normal human blood serum in a necessary amount in a similar manner to Example 1, and the resulting mixture was used as a sample. *Escherichia coli*: about $10^8$ cells.

2) Reagent
   I: reaction solution 1: 1 M glycine-NaOH pH 11.0
   II: reaction solution 2: 3 M magnesium chloride solution
   III: dispersion solution: 1 M glycine-HCl pH 5.0
3) Cationic Graft Polymer The above (5) graft polymer of epoxy octane-modified polyallylamine and diallyl dimethyl ammonium chloride (PAAEpo-g-DADMAC) was used.

Separation of *Escherichia coli* and confirmation of survival (viability) thereof were performed as follows.

500 μL of a sample, 100 μL of the above graft polymer, 100 μL of reaction solution 1, and 200 μL of reaction solution 2 were mixed. The sample and the above graft polymer were mixed. Thereafter, 20 μL of latex beads produced by a known method, for example, polystyrene latex LE (average particle diameter: 120 nm, manufactured by Nittobo Medical Co., Ltd.) was added and mixed well. Thereafter, the resulting mixture was centrifuged for 30 seconds by a tabletop small centrifugal machine to obtain a precipitation pellet. The supernatant was transferred to another centrifugation tube, and was further centrifuged at 15000 rpm for five minutes. The resulting precipitate was dispersed in 500 μL of a dispersion solution.

The precipitation pellet obtained by removing the supernatant was completely dispersed with 500 μL of a dispersion solution to obtain a suspension.

Each of 50 μL of the suspension derived from the supernatant and 50 μL of the suspension derived from the precipitation pellet was applied onto a LB bacteria culture agar medium, and was cultured at 37° C. for 18 hours. Viability of *Escherichia coli* was confirmed by formation of a colony.

2. Result

In a case where the graft polymer was mixed with the latex beads in advance, the bacterial cell was captured in a similar manner to a case where the latex beads were added after a reaction with a bacterial cell (FIG. 13).

Example 12

Confirmation of Survival (Viability) of Separated *Escherichia coli*

1. Method
1) Sample

*Escherichia coli* produced using the GFP expression Kit manufactured by Bio-Rad Laboratories, Inc. was added to normal human blood serum in a necessary amount in a similar manner to Example 1, and the resulting mixture was used as a sample. *Escherichia coli*: about $10^8$ cells 2) Reagent
   I: reaction solution 1: 1 M glycine-NaOH pH 11.0
   II: reaction solution 2: 3 M magnesium chloride solution
   III: dispersion solution: 1 M glycine-HCl pH 5.0
3) Cationic Graft Polymer The above (11) graft polymer of glycidol-modified polydiallylamine and diallyl dimethyl ammonium chloride was used.

Specifically, water was added to diallylamine such that the concentration became 79% by mass, and glycidol (1 equivalent with respect to amine) was dropwise added thereto while the solution was cooled with ice water and was stirred. After dropwise addition, the solution was allowed to react at 45° C. for 24 hours, and then was concentrated to obtain glycidol-modified diallylamine as an aqueous solution.

To 78% by mass glycidol-modified diallylamine, 35% by mass hydrochloric acid (1 equivalent with respect to amine) was added. Thereafter, water was added thereto such that the concentration became 50% by mass. The resulting solution was heated to 60° C., 2,2'-azobis(2-methyl propionamidine) dihydrochloride (6 mol % with respect to monomer) was added thereto dividedly, and polymerization was performed for 24 hours. The resulting solution was purified by electrodialysis to obtain glycidol-modified polydiallylamine as an aqueous solution. Water was added to 43% by mass glycidol-modified polydiallylamine prepared such that the concentration became 30% by mass, and the resulting solution was stirred at 20° C. Subsequently, each of 65% by mass diallyl dimethyl ammonium chloride (3 equivalents with respect to amine) and 36.04 g of 28.5% by mass APS aqueous solution (10 mol % with respect to monomer) was added thereto dividedly, and polymerization was performed for 24 hours. Thereafter, 36.04 g of 28.5% by mass APS aqueous solution (10 mol % with respect to monomer) was further added thereto dividedly, and polymerization was performed at 50° C. for 24 hours to obtain a graft polymer of glycidol-modified polydiallylamine and diallyl dimethyl ammonium chloride as an aqueous solution.

The above graft polymer and latex beads produced by a known method were mixed such that the graft polymer had a final concentration of 8% and the latex beads, for example, polystyrene latex LE (average particle diameter: 120 nm, manufactured by Nittobo Medical Co., Ltd.) had a final concentration of 5% to obtain a graft polymer solution.

In addition, the above (3) graft polymer of propylene oxide-modified polyallylamine and styrene (PAA-g-PSt) used in Example 1 was used as a positive control.

Separation of *Escherichia coli* and confirmation of survival (viability) thereof were performed as follows.

500 μL of a sample, 100 μL of the above graft polymer, 100 μL of reaction solution 1, and 200 μL of reaction solution 2 were mixed. Thereafter, the resulting product was centrifuged for 30 seconds by a tabletop small centrifugal machine to obtain a precipitation pellet. The supernatant was transferred to another centrifugation tube, and was further centrifuged at 15000 rpm for five minutes. The resulting precipitate was dispersed in 500 μL of a dispersion solution.

The precipitation pellet obtained by removing the supernatant was completely dispersed with 500 μL of a dispersion solution to obtain a suspension.

Each of 100 μL of the suspension derived from the supernatant and 100 μL of the suspension derived from the precipitation pellet was added to 5 mL of a LB medium, and was cultured at 37° C. for 18 hours. For confirmation of survival of *Escherichia coli*, an absorbance of each of the culture samples before and after the culture was measured using a spectrophotometer, and a change amount thereof was used as the amount of *Escherichia coli*.

Each of 50 μL of the dispersion solution derived from the supernatant and 50 μL of the dispersion solution derived from the precipitation pellet was applied onto a LB bacteria culture agar medium, and was cultured at 37° C. for 18 hours. Viability of *Escherichia coli* was confirmed by formation of a colony (FIG. 14).

As a control, a case containing polystyrene latex LE but not containing the above graft polymer was examined 2. Result

TABLE 13

| kind of polymer | pellet | | | sup | | | pellet/sup Δ | recovery (%) |
|---|---|---|---|---|---|---|---|---|
| | before culture | after culture | Δ | before culture | after culture | Δ | | |
| DAAGly-g-DADMAC + latex | 0.69 | 1.55 | 0.86 | 0.69 | 0.75 | 0.06 | 13.8 | 46.4 |
| only latex (negative control) | 0.04 | 0.07 | 0.03 | 0.04 | 0.09 | 0.05 | 0.7 | 1.8 |
| PAA-g-PSt (positive control) | 0.36 | 1.45 | 1.09 | 0.09 | 0.14 | 0.05 | 21.8 | 59.0 |

Example 13

Measurement Using Mass Spectrometry

1. Method

1) Sample

*Escherichia coli* produced using the GFP expression Kit manufactured by Bio-Rad Laboratories, Inc. was added to normal human blood serum in a necessary amount in a similar manner to Example 1, and the resulting mixture was used as a sample. *Escherichia coli*: about $10^8$ cells.

2) Reagent

I: reaction solution 1: 1 M glycine-NaOH pH 11.0

II: reaction solution 2: 3 M magnesium chloride solution

III: dispersion solution: 70% formic acid

IV: aggregation solution: 100% acetonitrile

3) Cationic Graft Polymer

The above (11) graft polymer of glycidol-modified polydiallylamine and diallyl dimethyl ammonium chloride used in Example 12 was used.

The above graft polymer and latex beads produced by a known method were mixed such that the graft polymer had a final concentration of 8% and the latex beads, for example, polystyrene latex LE (average particle diameter: 120 nm, manufactured by Nittobo Medical Co., Ltd.) had a final concentration of 5% to obtain a graft polymer solution.

In addition, the above (3) graft polymer of propylene oxide-modified polyallylamine and styrene (PAA-g-PSt) used in Example 1 was used as a positive control.

Separation of *Escherichia coli* and measurement using the mass spectrometry were performed as follows.

500 μL of a sample, 50 μL of the above graft polymer, 100 μL of reaction solution 1, and 200 μL of reaction solution 2 were mixed. Thereafter, the resulting product was centrifuged for 30 seconds by a tabletop small centrifugal machine to obtain a precipitation pellet.

The supernatant was removed, and the resulting precipitation pellet was completely dispersed with 30 μL of a dispersion solution. Subsequently, 100 μL of an aggregation solution was mixed therewith, and then the resulting mixture was centrifuged for 60 seconds by a tabletop small centrifugal machine The resulting supernatant was used as a sample for measurement using the mass spectrometry. The mass spectrometry was handled in a similar manner to Example 3.

As a control, a case containing polystyrene latex LE but not containing the above graft polymer was examined 2. Result

TABLE 14

| kind of polymer | score |
|---|---|
| DAAGly-g-DADMAC + latex | 2.13 |
| only latex (negative control) | <0 |
| PAA-g-PSt (positive control) | 2.10 |

It has been revealed from measurement using the mass spectrometry that *Escherichia coli* can be captured/collected without addition of reaction solution 2 (magnesium ion) when a mixed solution of a graft polymer of glycidol-modified polydiallylamine and diallyl dimethyl ammonium chloride and latex beads is used.

TABLE 15

| reaction solution | score |
|---|---|
| no use of reaction solution 2 (i.e., without magnesium ion) | 1.86 |
| use of reaction solution 2 (i.e., with magnesium ion) | 2.13 |

Example 14

Confirmation of Survival (Viability) of Separated *Escherichia coli*

1. Method

1) Sample

*Escherichia coli* produced using the GFP expression Kit manufactured by Bio-Rad Laboratories, Inc. was added to normal human blood serum in a necessary amount in a similar manner to Example 1, and the resulting mixture was used as a sample. *Escherichia coli*: about $10^8$ cells.

2) Reagent

I: reaction solution 1: 1 M glycine-NaOH pH 11.0

II: reaction solution 2: 3 M magnesium chloride solution

III: dispersion solution: 1 M glycine-HCl pH 5.0

3) Cationic Graft Polymer

The above (11) graft polymer of glycidol-modified polydiallylamine and diallyl dimethyl ammonium chloride used in Example 12 was used.

Separation of *Escherichia coli* and confirmation of survival (viability) thereof were performed as follows.

500 μL of a sample, 100 μL of the above graft polymer, 100 μL of reaction solution 1, and 200 μL of reaction solution 2 were mixed. The sample and the above graft polymer were mixed. Thereafter, 20 μL of latex beads produced by a known method, for example, polystyrene latex LE (average particle diameter: 120 nm, manufactured by Nittobo Medical Co., Ltd.) was added and mixed well. Thereafter, the resulting mixture was centrifuged for 30 seconds by a tabletop small centrifugal machine to obtain a precipitation pellet. The supernatant was transferred to another centrifugation tube, and was further centrifuged at 15000 rpm for five minutes. The resulting precipitate was dispersed in 500 μL of a dispersion solution.

The precipitation pellet obtained by removing the supernatant was completely dispersed with 500 μL of a dispersion solution to obtain a suspension.

Each of 50 μL of the suspension derived from the supernatant and 50 μL of the suspension derived from the precipitation pellet was applied onto a LB bacteria culture agar medium, and was cultured at 37° C. for 18 hours. Viability of *Escherichia coli* was confirmed by formation of a colony.

2. Result

In a case where the graft polymer was mixed with the latex beads in advance, the bacterial cell was captured in a similar manner to a case where the latex beads were added after a reaction with a bacterial cell (FIG. 15).

INDUSTRIAL APPLICABILITY

The method of the present invention and the kit therefor are able to separate and purify a target more efficiently than a conventional method using an ion exchange polymer, and are able to detect the target even when the amount of presence of the target in a sample is extremely small.

The invention claimed is:

1. A method for separating and concentrating a target substance having the property of binding to a cationic graft polymer, comprising:

(1) step of bringing the cationic graft polymer into contact with a sample containing the target substance to make the target substance bind to the cationic graft polymer in a basic solution, thereby forming a bound complex of the cationic graft polymer and the target substance;

(2) step of separating the bound complex of the cationic graft polymer and the target substance; and (3) step of eluting the target substance from the bound complex, wherein the cationic graft polymer is a polyamine graft polymer obtained by polymerizing a polyamine derivative obtained by a reaction between (a) a polymer compound having at least one amino group and (b) a compound having at least one epoxy group, and (c) an ethylenically unsaturated monomer.

2. The method according to claim 1, wherein in step 1, the basic solution further comprises a divalent or trivalent metal ion.

3. The method according to claim 1, further comprising a step for washing the bound complex after step (2) and before step (3).

4. The method according to claim 1, wherein the cationic graft polymer is fixed to a solid phase surface.

5. The method according to claim 1, further comprising a step for aggregating the cationic graft polymer that is not bound to the target substance in step (3).

* * * * *